United States Patent
Lim

(10) Patent No.: US 11,633,621 B2
(45) Date of Patent: Apr. 25, 2023

(54) SYSTEM AND METHOD FOR AUTOMATED PERSONALIZED BRAIN MODULATION WITH PHOTOBIOMODULATION

(71) Applicant: Lew Lim, Toronto (CA)

(72) Inventor: Lew Lim, Toronto (CA)

(*) Notice: Subject to any disclaimer, the term of this patent is extended or adjusted under 35 U.S.C. 154(b) by 98 days.

(21) Appl. No.: 16/640,682

(22) PCT Filed: Sep. 13, 2018

(86) PCT No.: PCT/IB2018/057005
§ 371 (c)(1),
(2) Date: Feb. 20, 2020

(87) PCT Pub. No.: WO2019/053625
PCT Pub. Date: Mar. 21, 2019

(65) Prior Publication Data
US 2020/0360715 A1 Nov. 19, 2020

Related U.S. Application Data

(60) Provisional application No. 62/560,058, filed on Sep. 18, 2017.

(51) Int. Cl.
*A61N 5/06* (2006.01)
*A61B 5/00* (2006.01)
(Continued)

(52) U.S. Cl.
CPC .......... *A61N 5/0618* (2013.01); *A61B 5/0006* (2013.01); *A61B 5/0075* (2013.01);
(Continued)

(58) Field of Classification Search
CPC .. A61N 5/0618; A61N 5/0603; A61N 5/0622; A61N 2005/0607;
(Continued)

(56) References Cited

U.S. PATENT DOCUMENTS

2016/0082268 A1* 3/2016 Hershey ............... A61N 1/0551
607/46
2017/0095670 A1* 4/2017 Ghaffari .................. G16H 20/30
(Continued)

FOREIGN PATENT DOCUMENTS

WO 2016130843 A1 8/2016
WO WO-2016130843 A1 * 8/2016 ......... A61N 1/36096
(Continued)

OTHER PUBLICATIONS

Choi, Richin, "International Search Report", International Application No. PCT/IB2018/057005, dated Dec. 17, 2018, 4 pages.
(Continued)

*Primary Examiner* — Carl H Layno
*Assistant Examiner* — Aya Ziad Bakkar

(57) ABSTRACT

A novel photobiomodulation (PBM) system and method that comprehensively directs therapeutic light energy into the brain from a combination of transcranial (through the skull) and intranasal (via the nasal channels) locations. In a preferred embodiment, the PBM device works in combination with a diagnostic tool to provide enhanced treatment of abnormal brain function intelligently, automatically, and unrestricted by geographical distances.

18 Claims, 20 Drawing Sheets

(51) Int. Cl.
*A61B 5/245* (2021.01)
*A61B 5/369* (2021.01)
*G16H 20/30* (2018.01)
*G16H 30/40* (2018.01)

(52) U.S. Cl.
CPC .............. *A61B 5/245* (2021.01); *A61B 5/369* (2021.01); *A61B 5/4836* (2013.01); *A61N 5/0603* (2013.01); *A61N 5/0622* (2013.01); *G16H 20/30* (2018.01); *G16H 30/40* (2018.01); *A61B 2576/026* (2013.01); *A61N 2005/0607* (2013.01); *A61N 2005/0626* (2013.01); *A61N 2005/0647* (2013.01); *A61N 2005/0653* (2013.01); *A61N 2005/0659* (2013.01); *A61N 2005/0663* (2013.01)

(58) Field of Classification Search
CPC .... A61N 2005/0626; A61N 2005/0647; A61N 2005/0653; A61N 2005/0659; G16H 20/30; A61B 5/369; A61B 5/245; A61B 5/0006; A61B 5/0075; A61B 5/4836; A61B 2576/026
See application file for complete search history.

(56) References Cited

U.S. PATENT DOCUMENTS

2017/0165485 A1* 6/2017 Sullivan ............... A61B 5/0022
2017/0258389 A1* 9/2017 Howard ............... A61B 5/4082

FOREIGN PATENT DOCUMENTS

WO        2016151377 A1    9/2016
WO   WO-2016151377 A1 * 9/2016 ........... A61N 5/0603

OTHER PUBLICATIONS

Choi, Richin, "Written Opinion of the International Searching Authority", International Application No. PCT/B2018/057005, dated Dec. 17, 2018, 6 pages.

* cited by examiner

| Variable | Day 0 | Treatment 1 | 2 | 7 | 14 | 21 |
|---|---|---|---|---|---|---|
| Eye contact | 1 | 1 | 9.2 | 9.8 | 9.8 | 9.8 |
| Demeanor | 1 | 1 | 3 | 5 | 7 | 8 |
| Motor skill - writing | 0 | 0 | 4 | 7 | 7 | 8 |
| Motor skill - other | 0 | 0 | 4 | 7 | 7 | 8 |
| Reading | 0 | 0 | 0 | 5 | 6 | 8 |
| Email | 0 | 0 | 0 | 4 | 7 | 8 |
| Orientation | 1 | 1 | 0 | 4 | 5 | 8 |
| Long term memory | 4 | 4 | 4 | 5 | 6 | 6 |
| Short term memory | 2 | 2 | 4 | 4 | 5 | 6 |
| Clarity | 4 | 4 | 5 | 6.5 | 6 | 6 |
| Critical and abstract thinking | 1 | 1 | 3 | 6 | 8 | 8 |
| Conversation | 1 | 1 | 4 | 6 | 6 | 7 |
| Mood | 1 | 1 | 3 | 4 | 7 | 8 |

FIGURE 11

SYSTEM AND METHOD FOR AUTOMATED PERSONALIZED BRAIN MODULATION WITH PHOTOBIOMODULATION

FIELD OF THE INVENTION

The present invention relates to a system and method for neurostimulation therapy, and in particular, to a system and method for automated personalized brain modulation with photobiomodulation.

BACKGROUND OF THE INVENTION

Many experts in brain treatments are of the view that there is a shortage of effective medications for many neurologic conditions and brain insults. These conditions may include traumatic brain injury (TBI), stroke, multiple sclerosis (MS), schizophrenia, autism, insomnia, post-traumatic stress disorder (PTSD), dementia and Alzheimer's disease (AD), Parkinson's disease (PD) and numerous other neurological conditions and insults. Some are of the view that the available medications are either no better than placebos or could even be harmful. As a result, many patients with neurological conditions and brain insults seek non-pharmacological therapies. Photobiomodulation is emerging as one of the credible ones.

Photobiomodulation (PBM):

Photobiomodulation (PBM), also known as low-level light therapy (LLLT), is a biostimulation technique that has shown promise in treating a number of conditions, including dementia and AD.

The biochemical mechanism of PBM interaction can be classified into direct and indirect effects. The direct effects include increasing the activity of ion channels such as the Na+/K+ ATPase and the indirect effects include regulating important secondary messengers such as calcium, cyclic adenosine monophosphate (cAMP) and reactive oxygen species (ROS)—all of which result in diverse biological cascades. These biological cascades lead to effects such as the maintenance of homeostasis and activating protective, anti-oxidant and proliferative gene factors, as well as the systematic responses, such as cerebral blood flow, which is deficient in neurocognitive disorders.

The most well investigated mechanism of action of PBM is its fundamental effect on mitochondrial function. PBM has been demonstrated to increase the activity of complexes in the electron transport chain of mitochondria, comprising complex I, II, III, IV and succinate dehydrogenase. In complex IV, the enzyme cytochrome c oxidase (CCO), functions as photo acceptor as well as transducer. CCO specifically accepts and transduces light in the red (620-700 nm) and the near-infrared (780-1110 nm) spectrums, wavelengths of lights which can be processed in PBM. The process increases the amount of ATP produced, as well as cyclic adenosine monophosphate (cAMP) and reactive oxygen species (ROS). The increase in ATP increases the activity of ion channels regulating cAMP and calcium, which results in the stimulation of diverse biological cascades and activate up to 110 genes for transcription, which lead to healing and recovery activities and the prolongation of the production of energy by the mitochondria. One of the most prominent responses to PBM is the activation of sodium pumps and the Na+/K+ ATPase, which leads to greater membrane stability and resistance to depolarization.

Modulations can also be presented in changes in the brain networks. Common techniques that observe these changes include functional magnetic resonance imaging (fMRI), functional near infrared spectroscopy (fNIRS) and electroencephalography (EEG). EEG is used to measure the electrophysiology signals involving the synchronization of oscillatory networks. They depend on interneuron activity which is believed to be influenced by PBM. Interneurons have widespread axonal plexus, and it's this widespread aspect that enables synchronous inhibition of multiple neurons within their circuits. Interneurons are connected by synapses which can be either chemical or electrical, and these synapses lead to synaptic inhibition transmitting powerful and synchronous rhythmic signals throughout entire networks. One of the most prominent ways of categorizing interneurons and their functions is by their expression of calcium-binding proteins and peptides. There are two main types of Ca2+-binding interneurons: parvalbumin (PV)— and cholecystokinin (CCK)-binding interneurons. PV interneurons are fast spiking and more consistent, involved in generating fast network oscillations whereas CCK interneurons are slower and much less reliable, with weaker contributions to network oscillations. Dysfunction of PV interneurons leads to reduced activity of gamma oscillations. On the other hand, the role of CCK interneurons in oscillations is hypothesized to be related to cell firing during theta oscillations.

In addition to increasing levels of ATP and cAMP, it has been observed that PBM results in an increase in nitric oxide (NO) levels, dissociated from CCO when photons are absorbed by CCO. The dissociation of NO from CCO leads to the enhancement of ATP production and acts as a vasodilator as well as a dilator of lymphatic flow, and can signal to activate a number of beneficial cellular pathways.

Neural Conditions Suitable for PBM Treatment:

There are many potential neural conditions that can benefit from light irradiation of one or more regions of the brain in-vivo. Whilst not proven at this time in large human randomized controlled trials, some small human studies suggest the potential of PBM treatment.

1. Treatment of Stroke, Neurotrauma, Cognition and an Emotional Mind State

Research studies have investigated brain irradiation for both stroke and neurotrauma. For example, recent studies have demonstrated that low energy light delivered transcranially was able to increase blood flow by 30%. Such demonstrated beneficial results with light irradiation have been accompanied with significant increases in nitric oxide production, a mechanism that is associated with the relaxation of vascular walls to achieve improved blood circulation. Thus, the cerebral blood flow was shown to be increased in both treated and untreated hemispheres. Also, subjects pretreated with light irradiation showed improved blood flow during the period of occlusion, with stable body temperature, heart rate and respiratory rates. The overall result is a significant decrease in apoptotic cells during a stroke event. Regular irradiation with low level near infrared red (NIR) light has also been found to be associated with significant neurological recovery after stroke events. Furthermore, these recovery effects were associated with increased neuronal proliferation and stem cell genesis and migration in the subventricular zone and hippocampal dentate gyri.

2. Treatment of Traumatic Brain Injury

Research studies have provided in-vivo evidence that the effects of low level light irradiation on cytochrome oxidase and the release of nitric oxide plays a major role in the neuroprotective action of light irradiation therapy not just against ischemia, but also against traumatic brain injury.

3. Treatment of Neurodegenerative Diseases

Light irradiation of the brain has been found to support neurogeneration in-vivo. Thus, light energy irradiation can potentially treat a range of different neurodegenerative diseases, such as Parkinson's disease (PD), Alzheimer's disease (AD) and Chronic Traumatic Encephalopathy (CTE). In a study using mice with PD symptoms, it was demonstrated that low level light irradiation at 670 nm wavelength helps prevent the loss of dopaminergic cells in the substantia nigra and improved behavior and functions. Improvements in AD symptoms are supported by improvements in biomarkers in animal studies and improvements in cognition and functions in human case studies.

4. Treatment of Depression and Other Emotional Deficits

Phenotypic expressions of mood disorders such as depression and post-traumatic stress disorder (PTSD) have been shown to be associated with decreased metabolic capacity in the prefrontal cortex region. Thus, light irradiation of the prefrontal cortex region may cause an increase of metabolic capacity in this region, as well as provide potential neuroprotection against these medical conditions. A pilot study showed that when the foreheads of human patients suffering from major depression and anxiety were irradiated with low level light of 810 nm wavelength, the blood flow to the frontal cortex increased and induced a 63% reduction in depression scores.

5. Treatment of Memory Deficits

Research studies have demonstrated that irradiation of the prefrontal cortex region of the brain with near-infrared light of 1072 nm wavelength improved an individual's functional memory. As this memory deficit condition is common among the more elderly, using light irradiation methods to treat the prefrontal cortex region of the brain can help with the aging-related problem of memory deficits.

6. Treatment of Dementia and Alzheimer's Disease

Neurodegeneration can lead to cognitive impairment that is often medically identified with dementia. One type of dementia, vascular dementia is identified with deficits in blood flow, and hence improving blood flow with PBM has the potential of treating it. The most common group of dementia is Alzheimer's disease (AD) which has a complex pathology that is still far from being established, involving multiple protein interactions and multiple genes. The early signs/symptoms of this neurodegenerative condition are revealed as regional brain metabolic deficits in the form of reduced cytochrome oxidase activity, an overt sign for potential risk of Alzheimer's disease. Because PBM of the brain activates cytochrome oxidase in brain cells, a transcranial PBM procedure can help alleviate the onset of AD.

Amyloid Cascade Hypothesis for Alzheimer's Disease:

Patients with AD have a build-up of amyloid-β (Aβ) in their brains which form the senile plaques is widely recognized as a pathological hallmark of AD. The transmembrane glycoprotein, amyloid precursor protein (APP) is metabolically processed to produce either amyloidogenic (ie. Aβ forming) or non-amyloidogenic products. Mutations in the APP gene and the genes that form the products that cleave APP (ie. secretase enzymes) play an important role in the amyloid cascade hypothesis. If the enzyme α-secretase cleaves APP proteolytically, a neuroprotective fragment called sAPPα is formed, preventing the formation of Aβ. However, if APP is sequentially cleaved by β-secretase and then γ-secretase, the formation of Aβ occurs. The apolipoprotein E (ApoE) type 4 has been identified as the most significant known risk factor for late-onset AD. The amyloid cascade hypothesis provided many drug targets for AD without success to date. When drugs were able to remove some of the amyloid plaque load, they did not translate into an improvement in symptoms of AD, and there are people with Aβ who have not developed AD symptoms. Although Aβ plaques have been recognized as a pathological hallmark of AD, the extent of their contribution to the disease is not clearly understood.

In addition to accumulation of senile plaques formed by the accumulation of Aβ, neurofibrillary tangles (NFT) are also characteristic of the pathology of AD. NFT are intracellular structures formed out of hyperphosphorylated microtubule-associated tau proteins. These proteins self-aggregate to become insoluble forms known as straight and paired helical filaments. The accumulation of tau in the neurons begins prior to the formation of NFT, suggesting that there is an early imbalance in the activity of protein kinases and phosphatases in AD. Several drug trials have focused on tau-based targets, including tau protein, tau phosphorylation, tau oligomerization, tau degradation and tau-based vaccination. To date, none of these trials have been successful. Meanwhile, its etiology with AD continues to be considered as important in AD research.

Mitochondrial Cascade Hypothesis for Alzheimer's Disease:

More recently, the mitochondrial cascade hypothesis of AD has been receiving increasing attention as a key mechanism explaining the pathogenesis of AD. The mitochondria are vital to neuronal function as they supply cellular energy, in the form of adenosine triphosphate (ATP). Furthermore, mitochondria provide the energy for synaptic plasticity, the mechanism by which the brain adapts to experience or use and encodes information at the synaptic level. Mitochondrial dysfunction is thought to play a key role in the impairments in synaptic plasticity seen in AD. They are found in abundance in synaptic terminals. Impairments in mitochondrial function are associated with synaptic dysfunction, decreased synaptic and neuronal outgrowth and apoptosis. Mitochondrial dysfunctions are well documented in the brains of patients with AD. Their dysfunction is a major cause for deficits in cerebral glucose metabolism that occurs in the brains of patients with AD, including brain regions associated with memory such as the hippocampus and entorhinal cortex. The deficits occur well in advance of presentations of the clinical symptoms. Mitochondrial dysfunctions observed in AD are also expressed as decreased mitochondrial enzyme activity, decreased activity of complexes of the respiratory chain and excessive levels of reactive oxygen species (ROS), producing increased oxidative stress.

It has been demonstrated that mitochondrial dysfunction can push APP processing towards the formation of Aβ production, suggesting that it is a factor driving the amyloid cascade. The presence of increased oxidative stress and slightly increased Aβ due to individual risk factors lead to mitochondrial dysfunction well before the formation of Aβ deposits. Increases in ROS over time result in further damage to mitochondria, resulting in a self-feeding feedback loop leading to increases in the production of Aβ and further mitochondrial damage. Furthermore, mitochondrial dysfunction has been found to produce inflammation and affect tau phosphorylation. The theory posits that mitochondrial dysfunction is the leading pathomechanism that causes neurodegeneration and AD-associated deficits.

Given the involvement of mitochondrial impairment as the key driving force underlying the decline seen in aging to AD, PBM therapies to counteract mitochondrial dysfunction in patients with AD holds promise as a treatment for the disease.

The Default Mode Network (DMN):

The Default Mode Network (DMN) of the brain has attracted interest because it has been associated with Alzheimer's disease, dementia, autism, schizophrenia, depression, chronic pain, Parkinson's disease, multiple sclerosis (MS) and post-traumatic stress disorder (PTSD). The DMN is active when individuals are engaged in internally focused mental activities including memory retrieval, envisioning the future, and conceiving the perspective of others. Regarding brain disorders, researchers have discovered targeted nexuses in the DMN, referred to as the "cortical hubs", often referred as "nodes", or sometimes identified as integral to "subdivisions", of the DMN. These hubs/subdivisions are highly connected in the DMN, although some of them may lie outside the network. It has been suggested that cortical hubs interconnect distinct, functionally specialized systems. These hubs/subdivisions include the ventral medial prefrontal cortex (vmPFC), the dorsal medial prefrontal cortex (dmPFC), the posterior cingulate cortex (PCC), the precuneus (PCu), the lateral parietal cortex (LPC) and the entorhinal cortex (EC). Through positron emission tomography (PET) amyloid imaging these hubs showed high amyloid-ß deposition in the locations consistent with the location of these hubs, suggesting the possibility that the hubs, while acting as critical way stations for information processing, may also augment the pathological cascade in AD. Experiments have shown that Aß deposition in Alzheimer's disease occurs preferentially in the locations of the cortical hubs. The vmPFC, dmPFC, PCC, PCu and LPC are reachable with 810 nm via light emitting diodes (LEDs) on selected locations on the scalp. The EC (including the hippocampal areas for memory processing) are reachable via a LED in the nasal cavity, a large part through the direct projections from the olfactory bulb located just above the nasal cavity.

Another important brain network may be the Salience Network (SN). Neurodegenerative illnesses such as AD and PD target the DMN, whereas behavioral variant disorders such as frontotemporal dementia (FTD) target the more anterior-located SN. While the DMN is identified with the whole brain, the SN emphasizes the frontal and anterior temporal lobes, anchored by the anterior insula and anterior cingulate cortex. While it appears that the DMN and SN may be different from each other, they are connected to each other in many activities. The SN plays an important role in driving the switches between the DMN and the Central Executive Network (CEN).

Photobiomodulation (PBM) can potentially stimulate brain cells in the lesions in the cortical hubs to heal. Researchers have found that cells repair themselves when they are exposed to low energy red light. The investigational data suggests that near infrared light irradiation protects the viability of cells and stimulates neurite outgrowth in cases of oxidative stress. Transgenic mice with AD recovered memory function and cognition function with transcranial PBM. An autopsy on the brains of these mice revealed a reduction of the lesions associated with the AD biomarkers, plaques and neurofibrillary tangles.

Neurological Disorders Associated with Lesions in the Cortical Hubs:

It has been proposed that lesions in the cortical hubs are associated with at least the following brain disorders: schizophrenia, AD, FTD, PD, temporal lobe epilepsy, Gilles de la Tourette syndrome, acute brain injury (coma), and migraine. Ischemia and oxidative stress are also identified with these lesions.

Diagnostic Tools Measuring Brain Activity:

Measuring the brain's activity and function has been possible with several safe but indirect measurements such as functional magnetic resonance imaging (fMRI), functional Near-Infrared Spectroscopy (fNIRS), Magnetoencephalography (MEG) and Electroencephalography (EEG).

Electroencephalography (EEG):

Electroencephalography (EEG) is a technique that measures the brain's electrical fields at the surface of the scalp and has been used over the years to study the brain's function. This electrical potential field yields a topographic distribution of voltage values, which mainly is the result of synchronous neuronal activity. The EEG device comprises one or more electrodes which are placed along the scalp. The electrodes measure voltage fluctuations resulting from ionic current within the neurons of the brain.

EEG exhibits oscillatory patterns that can be grouped into a few characteristic frequency bands. The EEG signal is characterized by its amplitude, phase and its spatio-temporal patterns. Commonly used and new advanced analysis techniques expose different features of EEG, and successfully link these to certain cognitive and neural functions of the brain: perception, memory, emotion, language, action, and other cognitive processes. Abnormal oscillations have been observed in many neurodegenerative and neuropsychiatric disorders and are even correlated with severity of symptoms. Neural oscillations are classified into 5 canonical frequency bands to describe different brain functions: delta, theta, alpha, beta and gamma oscillations.

Delta Oscillations: Delta oscillations are usually in the 1-3 Hz range. These rhythms are found in the thalamus of the brain and are associated with deep sleep. In contrast to the other oscillations, delta waves are enhanced in different neurodegenerative diseases where the function of interneurons is impaired. Another distinct characteristic of delta oscillation is their much more distant, indirect effects on cognitive function as compared to the other oscillations. Several evidences infer to the role of delta waves in silencing interferences from other, external neural networks during mental tasks. During the Go/No Go task, a paradigm in which participants must only respond to one stimulus (most commonly, by pressing a button) and must ignore all other stimuli, increased delta power is found in the central, parietal, and temporal regions of the brain.

Theta Oscillations: Theta bands have a frequency of approximately 4-7 Hz, are found in the hippocampus and are associated with dreaming sleep. Theta bands are activated and increased, in general, during the memory processes of encoding, retention and retrieval. Some examples include theta synchronization during memory tasks and theta desynchronization during semantic retrieval.

Alpha Oscillations: Alpha bands have frequencies ranging from 8-12 Hz and are typically found in the brain's posterior regions and central area. Alpha waves are seen in a relaxed but resting state, usually with the eyes closed. Alpha oscillations are most likely involved in the temporal fluctuations of neural network inhibition. Certain neural mechanisms have been shown to produce alpha oscillations, such as thalamocortical loops, rhythmically firing pyramidal cells, local interneurons and finally, interactions of synaptic inputs with different time constraints. Due to the fact that multiple and distinct neural mechanisms produce these frequencies, it suggests that there are many independent alpha generators in the brain. Changes in alpha activity are seen during tasks measuring long-term and short-term memory, as well as during the memory processes: encoding, retrieval and retention.

Beta Oscillations: Beta oscillation lies somewhere in the middle range of neural oscillation frequencies bands, usually at around 13-30 Hz. Beta waves are found in the brain's frontal regions and are associated with an alert and concentrated state. Out of the 5 types of oscillations, beta has traditionally been viewed as the least relevant to memory performance, with the exception of one type of task—beta power has been shown to decrease, along with an increase in theta power, during visual working memory tasks. Beta oscillations have been thought to be exclusively associated with motor and sensory processing, with research indicating they're not very much involved with memory and cognitive functioning. However, further studies report on recent, accumulating findings that indicate beta waves may actually play a supplementary role. It has been proposed that beta oscillation mediated ensemble formation within and between cortical areas, in accordance to a current task's demands. Similarly to the alpha, theta and gamma waves, beta waves also seem to increase during working memory maintenance. Beta synchronization seems to coincide with currently relevant task rules and stimulus categories. Specifically, typical changes in beta waves are seen late in the delay process of working memory maintenance—indicating that beta oscillations lead to the "reactivation" of cortical representations that are needed with the changing demands of a task.

Gamma Oscillations: Gamma oscillations have much higher frequencies, lying in the range of 30-50 Hz or more. Gamma bands are found in the somatosensory cortex of the brain, and associated brain states producing gamma bands, which are seen as sudden bursts of activity. Evidence from studies indicate that gamma bands are associated with memory encoding. For example, gamma power as well as spike gamma coherence in the hippocampus are both shown to be higher during successful encoding of information as opposed to unsuccessful encoding in monkey studies. Similar effects have been seen in human subjects, in the hippocampus and also in the cortical regions (somatosensory cortex). Gamma bands are related to working memory, as studies have reported increased gamma power with increasing number of items being held in memory during working memory tasks.

Abnormalities in brain oscillations are very common in neurological, neuropsychiatric and neurodegenerative conditions. Studies have reported increases in theta and delta activities and decreases in alpha and beta activities in patients with AD. During rest, a decrease of posterior alpha power is observed in patients with AD. This decrease in alpha power is correlated with severity of AD and cognitive impairments. Furthermore, in examining coherence, a measure of the degree of association between two frequency bands, a decrease in coherence between alpha and beta bands is also frequently found in patients with AD. Importantly, these abnormalities are correlated with the severity of the disease.

Other Diagnostic Tools:

Functional Near-Infrared Spectroscopy (fNIRS) is a non-invasive imaging method involving the quantification of chromophore concentration resolved from the measurement of near infrared (NIR) light attenuation or temporal or phasic changes. fNIR is sensitive to physiologic changes regarding the blood oxygenation in the brain and can be useful to locating abnormalities relating thereto. Such abnormalities have been linked to impaired cognitive function.

Functional magnetic resonance imaging (fMRI) measures brain activity by detecting changes associated with blood flow. This technique relies on the fact that cerebral blood flow and neuronal activation are coupled. Clinicians have used fMRI to map the brain's network activities and detect the effects of tumors, stroke, head and brain injury, or diseases such as AD, and developmental disabilities such as Autism.

Various diagnostic tools are being used to detect patterns indicative of neurological, neuropsychiatric and neurodegenerative conditions, such as abnormal brain oscillations detected by EEG. It would be advantageous to use this data detected by such diagnostic tools so that we can be more precise with the treatment of such conditions by PBM after adjusting various intervention parameters such as the pulse frequencies and power.

SUMMARY OF THE INVENTION

In one aspect, the present invention provides a system for performing non-invasive neurostimulation therapy of a living human brain of a subject, said non-invasive neurostimulation system comprising:

(A) one or more configured irradiation units, each of said one or more configured irradiation units comprising: a portable hollow casing having fixed dimensions, a sized internal spatial volume and an external surface configuration suitable for application to a skull of the subject, said portable hollow casing being comprised of a light energy transmitting material which forms at least a portion of the configured external surface of said portable hollow casing; and at least one light generating unit housed and contained within said sized internal spatial volume of said portable hollow casing of each configured irradiation unit and which is capable of generating light energy sufficient to irradiate the skull and penetrate through the skull to pass into the brain, whereby said one or more configured irradiation units emit the light energy after application to the skull and achieve passage of said emitted light energy into and through the skull into at least one portion of the brain in-vivo;

(B) a frame adapted for support of said one or more configured irradiation units and for at will placement of said light energy transmitting external surface of said one or more configured irradiation units at a fixed position and desired irradiation direction on the skull;

(C) a configured irradiation lens comprising: a portable hollow casing having fixed dimensions, a sized internal spatial volume, and an external surface configuration suitable for in-vivo insertion into a nasal cavity space of a nostril without causing substantial impairment to an ability of the subject to breathe and without invading nasal tissues of the subject, said portable hollow casing being comprised of a light energy transmitting material which forms at least a portion of the configured external surface of said portable hollow casing; and at least one light generating unit housed and contained within said sized internal spatial volume of said portable hollow casing and which is capable of generating light energy sufficient to penetrate through the nasal tissues and to pass into the brain, whereby said configured irradiation lens emits the light energy in any desired direction within the nasal cavity after in-vivo insertion and achieve passage of said emitted light energy from the nasal cavity into at least one portion of the brain in-vivo;

(D) a self-administrable applicator means adapted for support of said configured irradiation lens and for at will placement of said light energy transmitting external surface of said portable hollow casing of said configured irradiation lens at a fixed position and desired irradiation direction within the nostril adjacent to an internal lining of the nasal cavity of the subject;

(E) a replenishable power source of direct electrical current; and (F) a portable controller assembly able to control delivery of the light energy from said one or more configured irradiation units and said configured irradiation lens into at least one portion of the brain in-vivo, said portable controller assembly comprising: (i) a receiving circuit for receipt of such direct electrical current as is transferred to the portable controller assembly from the power source; (ii) a central processing unit for controlling and directing the flow of such direct electrical current as is received by the receiving circuit; (iii) a delivery circuit for delivering such direct electrical current from the controller assembly to said one or more configured irradiation units and said configured irradiation lens; (iv) at least one connector in electrical communication with the power source for conveyance of such direct electrical current to the central processing unit; and (v) at least one connector in electrical communication with said one or more configured irradiation units for conveyance of such direct electrical current from said central processing unit to said one or more configured irradiation units and said configured irradiation lens, wherein the portable controller assembly controls the light energy emitted from said one or more configured irradiation units and said configured irradiation lens with respect to one or more operational parameters selected from the group consisting of wavelength, coherency, energy, power, radiant exposure, exposure time, wave type, pulse frequency, fraction protocol, duty cycle, light beam spot and light beam penetration distance.

In another aspect, the present invention provides a method for performing non-invasive neurostimulation therapy of a living human brain of a subject, said non-invasive neurostimulation method comprising the steps of:

obtaining a light energy-emitting system comprising:

(A) one or more configured irradiation units, each of said one or more configured irradiation units comprising: a portable hollow casing having fixed dimensions, a sized internal spatial volume and an external surface configuration suitable for application to a skull of the subject, said portable hollow casing being comprised of a light energy transmitting material which forms at least a portion of the configured external surface of said portable hollow casing; and at least one light generating unit housed and contained within said sized internal spatial volume of said portable hollow casing of each configured irradiation unit and which is capable of generating light energy sufficient to irradiate the skull and penetrate through the skull to pass into the brain, whereby said one or more configured irradiation units emit the light energy after application to the skull and achieve passage of said emitted light energy into and through the skull into at least one portion of the brain in-vivo;

(B) a frame adapted for support of said one or more configured irradiation units and for at will placement of said light energy transmitting external surface of said one or more configured irradiation units at a fixed position and desired irradiation direction on the skull;

(C) a configured irradiation lens comprising: a portable hollow casing having fixed dimensions, a sized internal spatial volume, and an external surface configuration suitable for in-vivo insertion into a nasal cavity space of a nostril without causing substantial impairment to an ability of the subject to breathe and without invading nasal tissues of the subject, said portable hollow casing being comprised of a light energy transmitting material which forms at least a portion of the configured external surface of said portable hollow casing; and at least one light generating unit housed and contained within said sized internal spatial volume of said portable hollow casing of said configured irradiation lens and which is capable of generating light energy sufficient to penetrate through the nasal tissues and to pass into the brain, whereby said configured irradiation lens emits the light energy in any desired direction within the nasal cavity after in-vivo insertion and achieve passage of said emitted light energy from the nasal cavity into at least one portion of the brain in-vivo;

(D) a self-administrable applicator means adapted for support of said configured irradiation lens and for at will placement of said light energy transmitting external surface of said portable hollow casing of said configured irradiation lens at a fixed position and desired irradiation direction within the nostril adjacent to an internal lining of the nasal cavity of the subject;

(E) a replenishable power source of direct electrical current; and (D) a portable controller assembly able to control delivery of the light energy from said one or more configured irradiation units and said configured irradiation lens into at least one portion of the brain in-vivo, said portable controller assembly comprising: (i) a receiving circuit for receipt of such direct electrical current as is transferred to the portable controller assembly from the power source; (ii) a central processing unit for controlling and directing the flow of such direct electrical current as is received by the receiving circuit; (iii) a delivery circuit for delivering such direct electrical current from the controller assembly to said one or more configured irradiation units and said configured irradiation lens; (iv) at least one connector in electrical communication with the power source for conveyance of such direct electrical current to the central processing unit; and (v) at least one connector in electrical communication with said one or more configured irradiation units for conveyance of such direct electrical current from said central processing unit to said one or more configured irradiation units and said configured irradiation lens, wherein the portable controller assembly controls the light energy emitted from said one or more configured irradiation units and said configured irradiation lens with respect to one or more operational parameters selected from the group consisting of wavelength, coherency, energy, power, radiant exposure, exposure time, wave type, pulse frequency, fraction protocol, duty cycle, light beam spot and light beam penetration distance;

placing the light energy transmitting external surface of said one or more configured irradiation units at a desired fixed position adjacent to the skull of the subject such that light energy emitted by said one or more configured irradiation units will irradiate the subject's skull and penetrate through the subject's skull to pass into at least one portion of the brain in-vivo;

placing the light energy transmitting external surface of said configured irradiation lens within the nostril at a desired fixed position adjacent to the internal lining of the nasal cavity of the subject such that the light energy emitted by said configured irradiation lens will penetrate through the nasal tissues of the subject and pass into the at least one portion of the brain in-vivo;

controlling, by the portable controller assembly, said light generating units of said positioned configured irradiation units to generate the light energy sufficient to irradiate the subject's skull and penetrate through the subject's skull to pass into the brain; and controlling, by the portable controller assembly, said light generating units of said positioned configured irradiation lens to generate the light energy sufficient to penetrate through the nasal tissues and to pass into the brain.

BRIEF DESCRIPTION OF THE DRAWINGS

The present invention may be better understood and more readily appreciated when taken in conjunction with the accompanying drawings, in which:

FIG. 11 is a table showing changes in selected ordinal categorical normal functioning variables for a patient in Study No. 2;

DETAILED DESCRIPTION OF THE PREFERRED EMBODIMENTS

Figure 1:
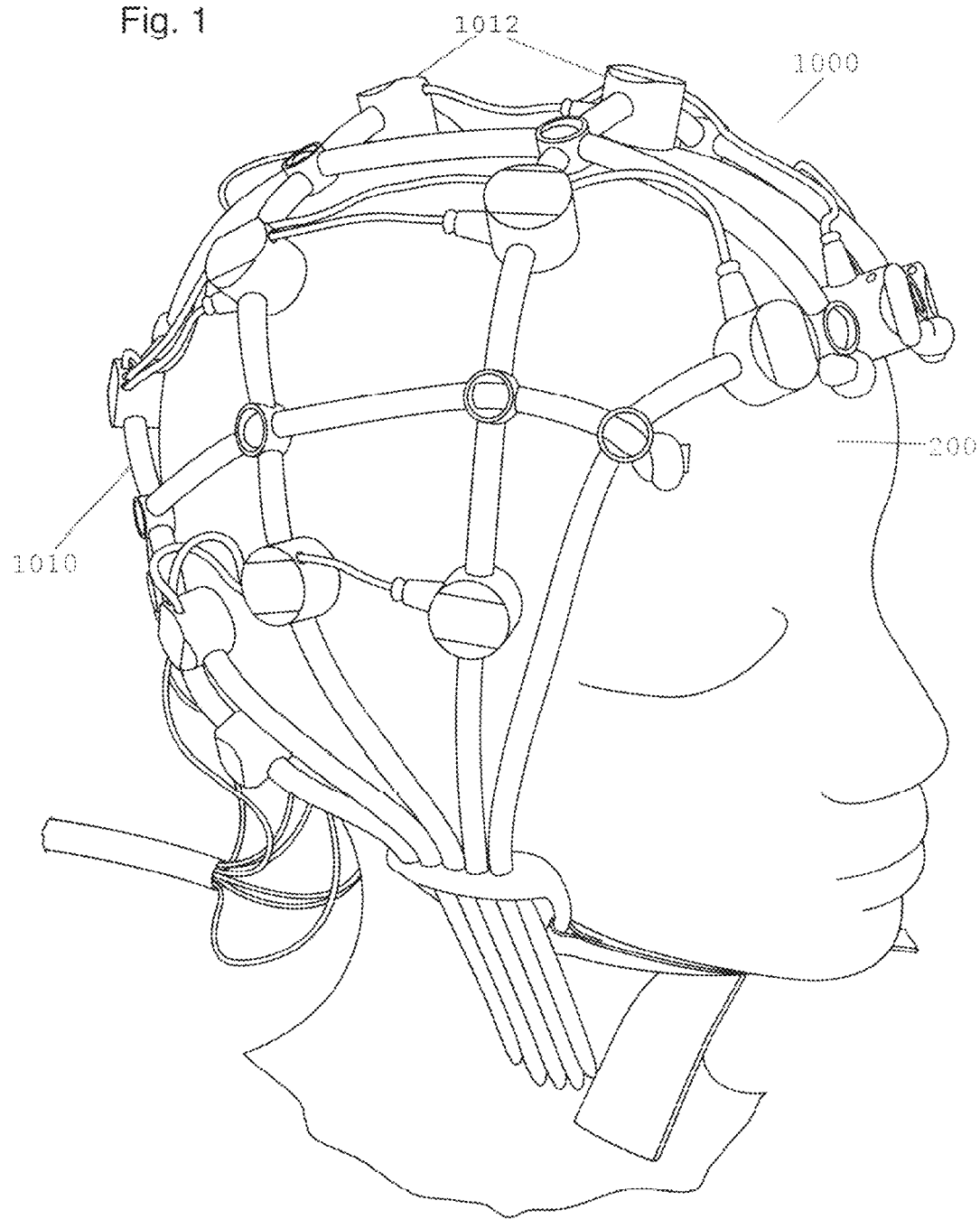
FIG. 1 is a perspective view of an exemplary Electroencephalography (EEG) device applied to a subject that can be used as a part of a preferred embodiment of a system of the present invention.

The invention concerns novel systems, apparatus and methods to stimulate therapeutic outcomes by irradiating the various parts brain (or neurostimulation) with light. The present invention provides a novel PBM system or apparatus that comprehensively directs therapeutic light energy into the brain from a combination of transcranial (through the skull) and intranasal (via the nasal channels) locations through modules and applicators containing light emitting diodes (LEDs) or other but not limited to, light transmission devices such as optic fibers, lasers or organic light emitting diodes (OLEDs). The irradiating light may be untargeted (i.e., broadly directed to stimulate the general brain area) or, preferably, be purposefully targeted at specific regions of the brain in order to achieve particular therapeutic outcomes. The coverage area and depth of light stimulation is influenced by selecting the appropriate parameters such as wavelength, coherency/synchrony, energy (Joules (J)), Power (Watts (W) or milliwatts (mW)) or irradiance (W/cm$^2$), radiant exposure or dose or fluence (J/cm$^2$), exposure time (seconds), wave type (continuous or pulse), frequency (Hertz (Hz)), duty cycle (percentage), fraction protocol (number of patient treatment sessions), light beam spot (area of landed beam), and light beam penetration (delivery) distance.

In another aspect, the present invention provides a system and method whereby the PBM device of the present invention works in combination with a diagnostic tool to provide enhanced treatment of abnormal brain function. The diagnostic tool may be, for example, an electroencephalography (EEG) device, a functional Near-Infrared Spectroscopy (fNIRS) device or functional magnetic resonance imaging (fMRI) equipment. As a specific example, an EEG device may be used to detect abnormal brain function in a patient. This patient-specific data is processed by a software application on a smartphone, smartwatch, tablet computer, laptop computer, desktop computer or any appropriate computing device. The system of the present invention is then directed to provide light energy with specific parameters and targeted to specific brain locations which are considered suitable for treatment of this patient's particular abnormalities. In this manner, automated personalized brain modulation is provided. Thus, the present invention provides a system and method which combines: (i) a diagnostic tool which detects abnormal brain function in a subject; (ii) one or more computer applications which process data regarding the abnormal brain function and utilize this data to set appropriate parameters for the light energy to be directed to the brain of the subject; and (iii) a device for directing the light energy with set parameters to the brain of the subject. The present invention also includes aspects whereby the specific parameters in using the diagnostic tool and/or the PBM device of the present invention can be manually manipulated for selective PBM.

Targeted Transcranial Light Therapy of the Present Invention:

The present invention provides targeted treatment of specific areas of the brain, such as the cortical hubs of the default mode network (DMN) or another network such as the Salience Network (SN) or the Central Executive Network (CEN). Since the cortical hubs are highly connected with each other (sometimes labelled as "connectomes", "nodes" or "subdivisions"), stimulating a few of these major hubs may stimulate the whole network in a holistic manner. This allows a light-weight, portable transcranial NIR light therapy device to be designed, pointing at a few select locations, instead of the less comfortable closed helmet previously used in transcranial light therapy research. Specifically, the present invention provides a light frame which supports one or more cluster heads, wherein each cluster head houses one or more light generating units. The light energy-emitting apparatus comprises at least one configured irradiation unit including a portable hollow casing having fixed dimensions, a sized internal spatial volume, and an external surface configuration suitable for application to the skull. The system and apparatus are designed such that light energy is delivered through the skull using a headset that is easy to apply to the subject's head and comfortable to wear for an extended period of time. Each configured irradiation unit is preferably positioned within the frame such that, when the headset is worn by the subject, light energy can be directed to specific targets, such as cortical hubs of the DMN The present invention preferably targets selected locations of the DMN because these anatomical regions are associated with AD and a wide variety of other brain conditions. In the treatment, a preferred set of transcranial targets for the present invention include but are not limited to: the cortical hubs of the DMN, which include the ventral medial prefrontal cortex (vmPFC), the dorsal medial prefrontal cortex (dmPFC), the posterior cingulate cortex (PCC), the precuneus (PCu), the lateral parietal cortex (LPC), the entorhinal cortex (EC), the dorsal-lateral prefrontal cortex (DLPC), the cerebellum and/or brain stem. The apparatus or device of the present invention can also reach relatively deeper areas of the brain associated with Parkinson's disease such as the basal ganglia, substantia nigra, subthalamic nucleus and globus palidus. Selected modules may be exclusively turned on for specific treatment, say targeting the cerebellum only.

Intranasal Photobiomodulation of the Present Invention:

The present invention also preferably delivers therapeutic light irradiation to the brain through the tissues lying adjacent to the nasal cavity. For this purpose, the light energy-emitting apparatus comprises a configured irradiation lens including a portable hollow casing having fixed dimensions, a sized internal spatial volume, and an external surface configuration suitable for in-vivo insertion into the nasal cavity space of a nostril. The nasal insertion apparatus components are designed to be small and comfortable; and to avoid causing significant or meaningful impairment in the user's ability to breathe. After insertion, the apparatus may be adjusted or preset to direct the irradiating angle of the release of the light emitted from the apparatus, set the desired power levels, generate a pulse frequency for the emitted light, and choose the time duration for the treatment session in order to achieve the intended therapeutic effects.

A light source that is inserted into the nasal cavity will anatomically lie in close proximity (about 1 inch) to the olfactory bulb and (about 3 inches of mainly air cavity and soft tissue) to the mid-brain area. When the light source in this intranasal position is pointed towards the brain, little energy is required for effective light irradiation because much of the physical pathway distance to the brain tissue is the air cavity of the nostril. Mid-brain areas include the amygdala, the hippocampus, the hypothalamus, the septal area and the cingulated cortex. A portion of the neo-cortex region that is easily illuminated by the light source is the prefrontal cortex. In one embodiment, preferred intranasal targets include but are not limited to the ventral prefrontal cortex, entorhinal cortex and parahippocampal area (including the hippocampus). These targets may be critical in the treatment of AD.

Components of the System/Apparatus:

The non-invasive system and apparatus of the present invention comprises at least the following component parts:
(i) a portable hollow casing;
(ii) a light generating unit which is housed and contained within the interior spatial volume of the hollow casing;
(iii) a source of electrical current;
(iv) a process controller assembly; and
(v) optionally, a smart phone, tablet computer or other computing device.

These components may preferably be electrically linked together by at least one connector for transfer of direct electrical current from the source of electrical current to the controller assembly, and at least one connector for conveyance of direct electrical current from the controller assembly to the light generating unit.

1. A Portable Hollow Casing

The present invention includes at least one portable hollow casing having fixed dimensions, a sized internal spatial volume and an external surface configuration suitable for application to the head and/or in-vivo insertion into the nasal cavity space of a nostril. The intended purposes and goals of the portable casing are twofold: (i) to serve as a containment chamber that is configured for easy application to the skull and/or in-vivo insertion into the nasal cavity space of a nostril; and (ii) to act as a molded lens that reflects and directs emitted light waves to the brain.

Preferably, the portable casing may be constructed and formed of a light transmitting material over at least a portion of its external surface, and will encompass that volumetric zone intended for housing and containment of at least one light generating unit. By definition, such light transmitting material includes and encompasses transparent, translucent and opaque matter. However, in most instances, a completely clear and transparent matter is preferred.

For intranasal photobiomodulation in the present invention, the portable hollow casing must have dimensions which are small enough to allow insertion into one nostril, will minimize impairment of the subject's ability to breathe, and yet will be able to maximize the scattering of the light particles towards the walls of the subject's nasal cavity. For these reasons, it is very desirable that the hollow casing for intranasal therapy be fashioned in size and configuration for support by a tangible holder or fixture which the human subject can hold with his fingers. Thus, while the portable casing can be fashioned into any generally slender and elongated shape such as a tubular, or cigar-shaped, or cylindrical format, it is deemed both useful and appropriate that the overall configuration of the portable hollow casing also provide a structural means for support which allows its placement into a nasal cavity space at will. For this reason also, the "L" shaped format is very desirable.

2. The Light Generating Unit(s)

The light generating unit will be able to deliver therapeutic light at wavelengths that include but are not necessarily limited to the following: (i) in the visible color spectral ranges, the visible red light wavelengths ranging between about 620-780 nm; and (ii) in the non-visible spectral ranges, the near-infrared light wavelengths ranging between about 780-1400 nm. In addition, the generated light energy waves and particles may alternatively be: (i) either coherent (as in lasers) or non-coherent (as in non-laser light emitting diodes (LEDs); (ii) be either pulsing or non-pulsing (continuous wave) in delivery; (iii) be either constant or non-constant in intensity; (iv) be either uniform or non-uniform in phase; (v) polarized and non-polarized; and (vi) have a regular or irregular flux.

Any conventionally known means for generating electromagnetic radiation or articles for propagating radiant energy are acceptable for use in the present apparatus. In the majority of embodiments, it is intended and expected that either a low level laser unit or a LED will be employed as the light generating unit(s) for irradiating purposes.

3. A Source of Electric Current

It is preferred that a portable and replenishable source of on-demand direct electrical current exist as a component part of the apparatus and system of the present invention. The therapeutic treatment system and method provided by the instant invention is intended to deliver a specific energy dosage (measured in Joules), which is a function of power (in wattage) and time (in seconds), and which is deemed to be efficacious for each therapeutic treatment.

The power supply typically will convey energy in the form of direct electric current. Adequate quantities of electric current can be repeatedly conveyed from, for example, a single battery source or from a combination of several dry cells joined together in series or parallel. In some other desirable embodiments, the source of electric power will be in the form of a rechargeable power bank, a direct current battery unit (rechargeable from ordinary household alternating current receptacles) or as alternating current (AC) via a power adaptor. It is expected and intended that there will be several alternative embodiments with different combinations of these components and which would be suitable for different configurations of power, energy dosage and treatment time.

As to positioning, in some preferred embodiments, the power source is a discrete entity which is held and contained entirely within the internal confines of the controller assembly. In other preferred embodiments, however, the source of electric current can be a self-contained, separate and free standing unit which is in electrical communication with the controller assembly via an electrical cable and connector module linkage, such as a portable and rechargeable power bank. In an alternative embodiment, the source of electrical current is obtained by plugging the system and apparatus into the local electrical grid via a power adaptor.

4. Process Controller Assembly

The process controller assembly is a portable unit component having at least three structural features:
(i) A receiving circuit for receipt of such electrical current as is transferred to the controller assembly from the electrical current source;
(ii) A central processing unit (CPU) for controlling and directing the flow of such electrical current as is received by the controller assembly over time; and
(iii) A delivery circuit for delivering direct electrical current from the controller assembly to the light generating unit(s).

It is intended and expected that the process controller assembly will be electrically linked to other essential components of the apparatus and thus typically will also have:
(a) at least one connector for transfer of direct electrical current from the source of electrical current to the controller assembly; and
(b) at least one connector for conveyance of direct electrical current from the controller assembly to the light generating unit (s).

These connectors typically are formed as insulated copper wire cables and jack modules that allow for quick and easy linkage and electrical communication with both the electrical current source and the light generating unit(s).

It is intended and expected that any conventionally known and interchangeable electric cables and connectors will be used to link the controller assembly to the irradiation lens.

This also provides a distinct advantage and benefit to the user, namely the option to exchange one configured irradiation lens (able to transmit light at a first wavelength) for another irradiation lens (able to transmit light at a second and different wavelength), and thereby permits the use of different lasers and alternative light emitting diodes able to deliver different wavelengths of visible and invisible light energy with one single controller assembly.

The preferred process controller assembly is dimensionally small in size, light in weight, and portable. In one preferred embodiment, it has fixed dimensions which are no larger than an average shirt pocket (i.e., approximately 4.5 inches in length, by 4.5 inches in width, by 1 inch in depth), and is formed of a resilient material of moldable thermoplastic or of another material. Preferred embodiments of the controller assembly typically include a central processing unit (CPU) in a circuit board which is able to control and direct the flow of electric current in dosage, power, and time from the electrical source to the configured irradiation lens.

In some preferred embodiments, the source of electrical current lies internally and is contained within the interior spatial volume of the controller assembly, and appears as an electric battery (dry cell or rechargeable unit). In this instance, the controller assembly also has a socket adapted for the attachment of an insulated copper wire cable and modular jack connector, whose other end is joined to the light generating unit disposed within the hollow casing.

The central processing unit ("CPU") of the controller assembly is preferably able to regulate light energy with respect to many different parameters including but not limited to: wavelength, coherency/synchrony, energy (Joules (J)), Power (Watts (W) or milliwatts (mW)) or irradiance (W/cm$^2$), radiant exposure (J/cm$^2$), exposure time (seconds), wave type (continuous or pulse), frequency (Hertz (Hz)), duty cycle (percentage), fraction protocol (number of patient treatment sessions), light beam size (area of landed beam), and light beam penetration (delivery) distance.

The process controller assembly will not operate in the absence of a source of electrical current. In addition, the controller assembly, besides preferably switching off the unit after a predetermined time, is a circuitry which provides power to drive the light generating unit(s) properly and efficiently. The controller also ensures that the power delivered to the light generating unit(s) is consistent. It therefore desirably monitors the battery strength where the source is a power bank or battery, and switches off the unit if the power bank or battery is unable to supply sufficient power to drive the circuitry properly.

5. Smart Phone, Tablet Computer or Other Computing Device

In one alternative embodiment, the function of the controller assembly may be replaced, in whole or in part, by smartphone, smartwatch, tablet computer, laptop computer, desktop computer or any appropriate computing device. The smart phone, for example, may operate on one of the more popular mobile platforms, and which may include those from Apple™, Android™, Blackberry™ and Windows™. The light generating unit(s) could be connected via a cable or wirelessly to the smart phone. The smart phone carries a downloadable software application that would largely duplicate the software functions in the controller assembly. A modified attachment containing interface processing software in a computer chip will provide an interface between the existing applicator and the proprietary smart phone platform. With this embodiment, the user need not carry an additional or separate controller unit, and yet the software application will also contain more software controls and graphic interfaces. Alternatives to the smart phone include a smartwatch, tablet computer, laptop computer, desktop computer or any appropriate computing device with the software application downloaded thereon.

In yet another alternative embodiment, the controller assembly works in combination with smartphone, smartwatch, tablet computer, laptop computer, desktop computer or any appropriate computing device. In particular, the computing device has downloaded thereon a software application which can: (i) turn the controller assembly on and off; and/or (ii) transmit instructions to the controller assembly to adjust the light energy parameters of each individual light generating unit, including but not limited to wavelength, coherency/synchrony, energy (Joules (J)), Power (Watts (W) or milliwatts (mW)) or irradiance (W/cm$^2$), radiant exposure or dose or fluence density (J/cm$^2$), exposure time (seconds), wave type (continuous or pulse), frequency (Hertz (Hz)), duty cycle (percentage), fraction protocol (number of patient treatment sessions), light beam size (area of landed beam), and light beam penetration (delivery) distance.

Furthermore, the computing device can serve as a system interface where a user enters instructions through the interface to turn the controller assembly on and off and/or adjust the light energy parameters of each individual light generating unit. Instructions may be entered by any known input component such as a touch screen, mouse, keypad, keyboard, microphone, camera or video camera Once the user inputs instructions into the system interface, instructions are transmitted to the controller assembly which then adjusts the parameters of the light energy being delivered to by the light generating units.

In these embodiments, any conventionally known and interchangeable electric cables and connectors can be used to link the computing device to the controller assembly. Alternatively, the computing device may communicate with the controller assembly by wireless means. Connections between any of these components are implemented using appropriate wired or wireless communications via protocols such as BLUETOOTH™, Wi-Fi, Near Field Communications (NFC), Radio Frequency Identification (RFID), 3G, Long Term Evolution (LTE), Universal Serial Bus (USB) and other protocols and technologies known to those skilled in the art.

Diagnostic Tool as a Component of the Present Invention:

The system and method of the present invention may also comprise a tool for detecting abnormal brain function. The diagnostic tool may be, for example, a functional magnetic resonance imaging (fMRI) device, a functional Near-Infrared Spectroscopy (fNIRS) device, a Magnetoencephalography (MEG) device or an Electroencephalography (EEG) device.

The diagnostic tool performs the function of collecting data from a subject relating to brain function. The diagnostic tool is coupled to a smartphone, smartwatch, tablet computer, laptop computer, desktop computer or any appropriate computing device. These components are connected using appropriate wired or wireless communications via protocols such as BLUETOOTH™, Wi-Fi, Near Field Communications (NFC), Radio Frequency Identification (RFID), 3G, Long Term Evolution (LTE), Universal Serial Bus (USB) and other protocols and technologies known to those skilled in the art. Collected data is transmitted using this connection from the diagnostic tool to the computing device.

The computing device comprises a processor which performs functions and operations necessary for the operation of the device. To perform functions and operations, the processor uses data and applications stored in a storage component of the computing device. A communications component allows the computing device to communicate with external devices and networks. The computing device preferably comprises a display component for displaying data and information for a user to view. The computing device also preferably comprises an input component which allows the user to enter information and commands. For example, the input component may preferably be a touch screen, mouse, keypad, keyboard, microphone, camera or video camera. A touchscreen may preferably serve as both the display and the input component.

One of the applications stored on the computing device is an analysis software which can process and analyze the collected data. For example, an EEG analysis software would be used to process and analyze data collected by an EEG device. One preferred function of this application may be to process the collected data and display it in a viewable format on the display component of the computing device. Alternatively, the analysis application could transmit collected data, preferably via a network, to another computing device at a different or remote location where such collected data is displayed in a viewable format. The network may be wired or wireless, such as for example an Ethernet network, local area network, metropolitan area network or optical network.

Another function of the analysis software is to compare the data collected from the subject to data regarding brain function in normal subjects. In making this comparison, the analysis software produces analysis data of the subject's brain activity which may include detecting abnormal brain function in the subject. In alternative embodiments, the collected data is transmitted, preferably via a network, to another computing device at a different or remote location where such collected data is compared to data regarding brain function in normal subjects and the analysis data of the subject's brain activity is produced, possibly including the detection of abnormal brain function in the subject. The network may be wired or wireless, such as for example an Ethernet network, local area network, metropolitan area network or optical network.

Another application, specifically a PBM parameter-setting application, is used to: (i) receive, process and analyze the subject's collected data and/or the analysis data which may include the subject's abnormal brain function; (ii) in view of such data, select the appropriate parameters for the light energy to be administered to the subject in PBM treatment; and (iii) transmit instructions regarding the selected parameters to the controller assembly. The PBM parameter-setting application may be stored on the same or a different computing device as the above-mentioned analysis application. The analysis application may transmit the data directly to the PBM parameter-setting application or to a database where it is stored and then retrieved by the PBM parameter-setting application. Alternatively, the PBM parameter-setting application may retrieve the data directly from the analysis application or from the database. The database may preferably be on the same or a different computing device as either of the above-mentioned software applications. In any case, the subject's collected data and/or analysis data including the subject's abnormal brain function is received by the PBM parameter-setting application. The PBM parameter-setting application selects the appropriate parameters for the light energy to be administered to the subject in PBM treatment and then transmits instructions regarding the selected parameters to the controller assembly.

Through the controller assembly, the appropriate light energy parameters are administered to the subject.

In another preferred aspect, a subject's personal history, which may include the subject's collected data, analysis data which could include the subject's abnormal brain function and/or data regarding the subject's PBM treatment history, may be stored on a database. The database may preferably be on the same or a different computing device as either of the above-mentioned software applications.

In one preferred embodiment which uses an EEG device as a diagnostic tool, the system of the present invention may for example comprise:

1. An EEG device comprising a cap that contains one or more electrodes for reading and recording a subject's electrical brain activity. The electrodes are connected to and send data on the subject's electrical brain activity to an external device.

2. A computing device having EEG analysis software downloaded thereon, to which the above-mentioned EEG data is sent. The EEG analysis software compares the subject's EEG readings to normal EEG readings, and produces analysis data which may include detected abnormalities.

3. A PBM parameter-setting application that is downloaded to the same or a different computing device as the computing device which has the EEG analysis software downloaded thereon. The PBM parameter-setting application can be used to: (i) power on/off the controller assembly which is described below; and/or (ii) adjust the light energy parameters of the system, wherein these adjustments are preferably made in view of the EEG analysis data.

4. A system interface to transmit instructions regarding specific light energy parameters to the controller assembly which is described below. The same or a different computing device as the computing device which has the EEG analysis software and/or PBM parameter-setting application downloaded thereon can preferably serve as the system interface. Preferably, the system interface has an input component that can be used to manually control the one or more irradiation units via the controller assembly.

5. One or more frames or headsets preferably supporting one or more irradiation units, such that the one or more irradiation units can be positioned to target selected locations on the subject. In one preferred embodiment, the irradiation units are positioned on the skull to target the following: the dorsal medial prefrontal cortex (dmPFC); the posterior cingulate cortex (PCC); the precuneus (PCu) plus the lateral parietal cortex (LPC); left and right dorsal-lateral prefrontal cortex (DLPC); in the nasal cavity to target the ventral prefrontal cortex, entorhinal cortex and/or parahippocampal area (including hippocampus); and on the suboccipital area to target the cerebellum and/or brain stem. One or more irradiation units can alternatively target locations such as the vagus nerves on the neck, the ear lobe/canal and the eyes (preferably positioned inside an eye goggle), or any other parts of the body.

6. A controller assembly that delivers electrical current and instructions regarding specific light energy parameters to the one or more irradiation units, preferably automatically based on the EEG-based computer analysis or based on manual input. Preferably, the controller assembly has an input component that can be used to manually control the one or more irradiation units.

7. A source of electrical current, such as a rechargeable power bank or battery, which provides electrical current to the controller assembly. The rechargeable power bank is one preferred embodiment as it allows for portability of the system. Alternatively, the controller assembly can be powered by electricity directly from the electricity grid through a power adaptor.

Connections between any of these components are implemented using appropriate wired or wireless communications via protocols such as BLUETOOTH™, Wi-Fi, Near Field Communications (NFC), Radio Frequency Identification (RFID), 3G, Long Term Evolution (LTE), Universal Serial Bus (USB) and other protocols and technologies known to those skilled in the art.

The system can preferably have a set of default parameters for the light energy which are generally efficacious. These default parameters can be automatically modified in view of the analysis data. The default parameters can also preferably be modified manually through the system interface. The system can preferably generate a negative feedback loop at selected time intervals to trigger the delivery of modulating parameters.

Preferred System and Apparatus Embodiments of the Present Invention

Figure 2:
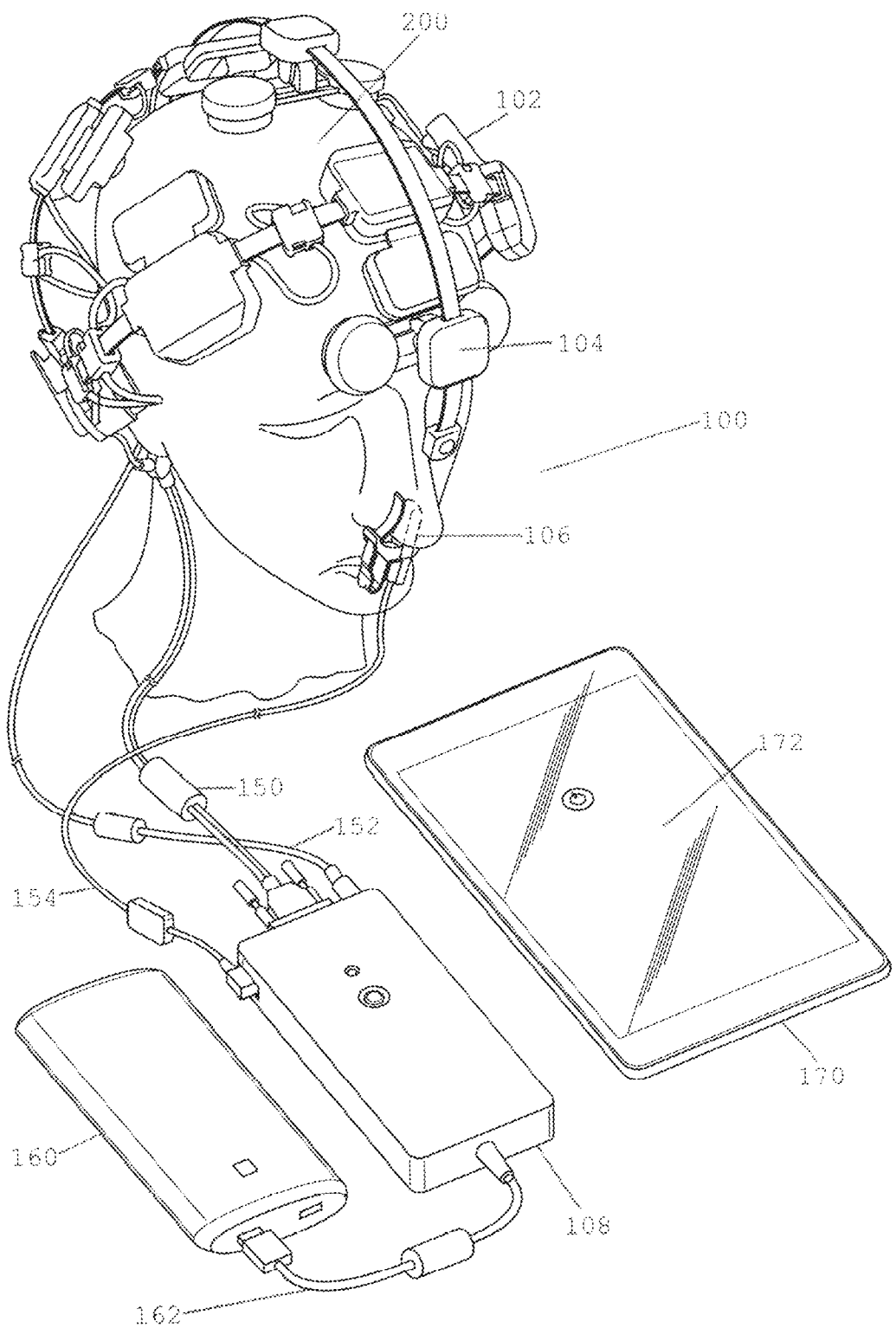
FIG. 2 is a perspective view of components of a preferred embodiment of a system of the present invention, including a transcranial photobiomodulation (PBM) headset, a secondary PBM headset, an intranasal PBM applicator unit, a controller assembly, a power bank and a tablet computer.
Figure 3:
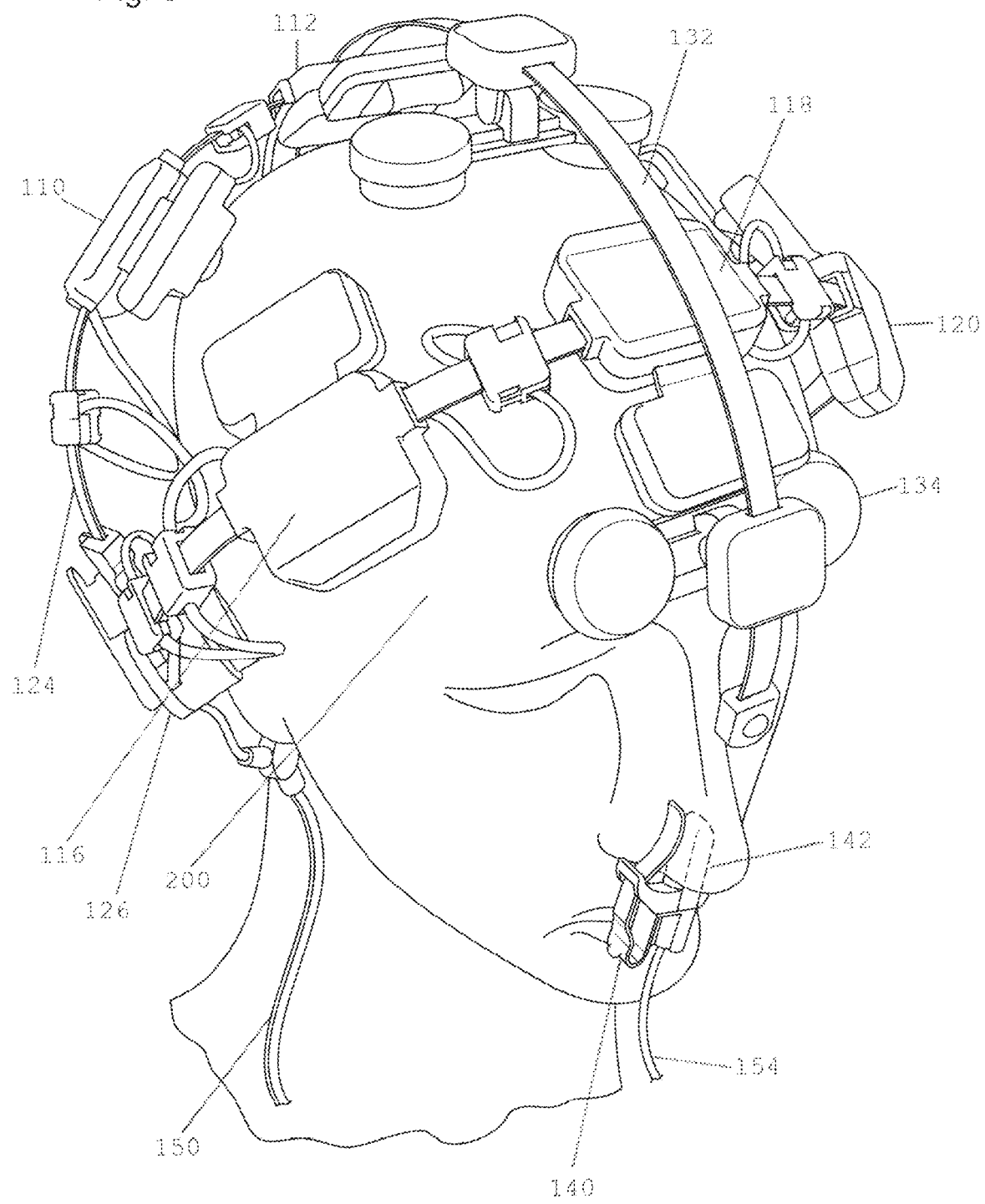
FIG. 3 is a perspective view of the transcranial photobiomodulation (PBM) headset, secondary PBM headset, and intranasal PBM applicator unit of FIG. 2 applied to a subject.
Figure 4:
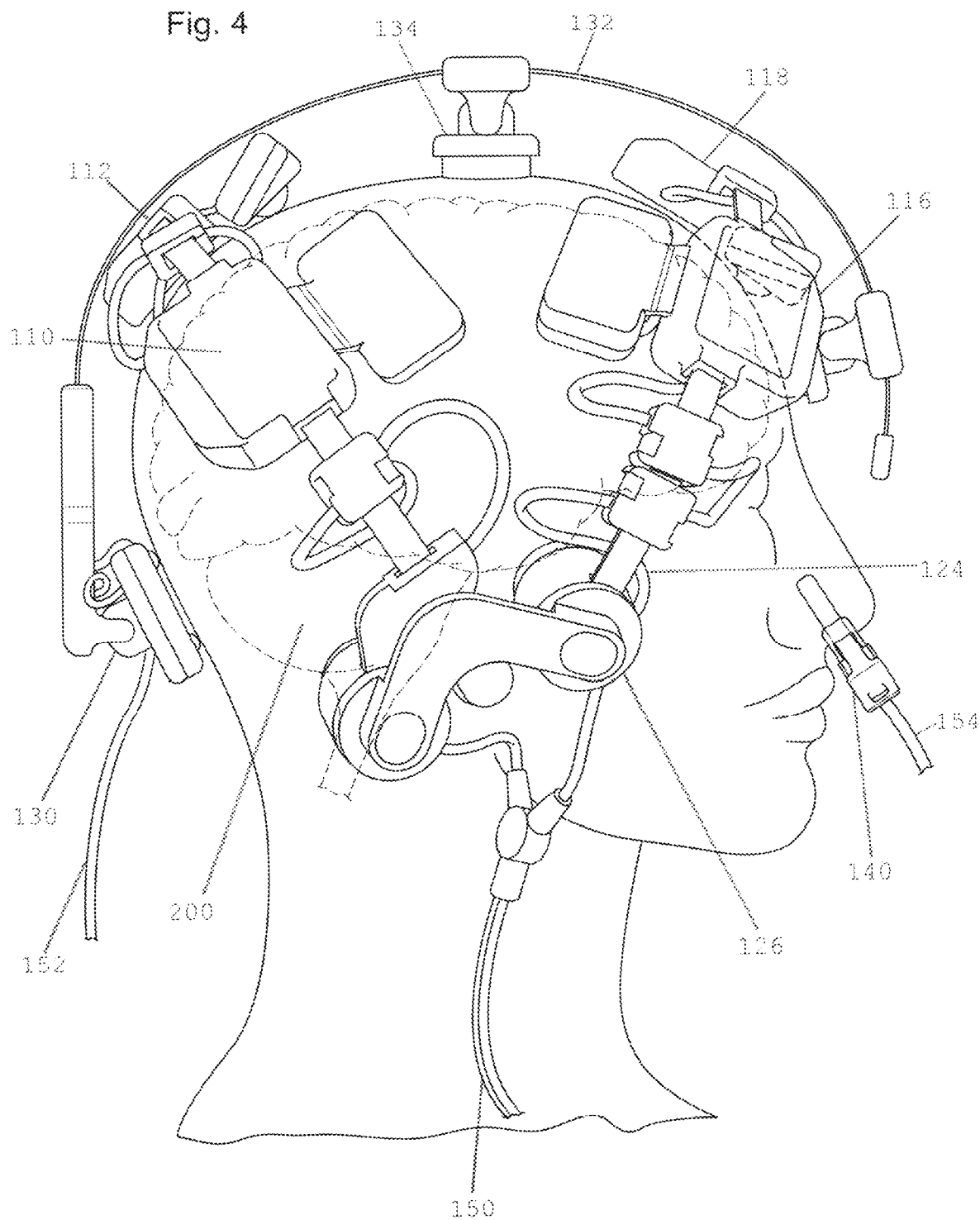
FIG. 4 is a side view of the transcranial photobiomodulation (PBM) headset, secondary PBM headset, and intranasal PBM applicator unit of FIG. 2 applied to a subject.
Figure 5:
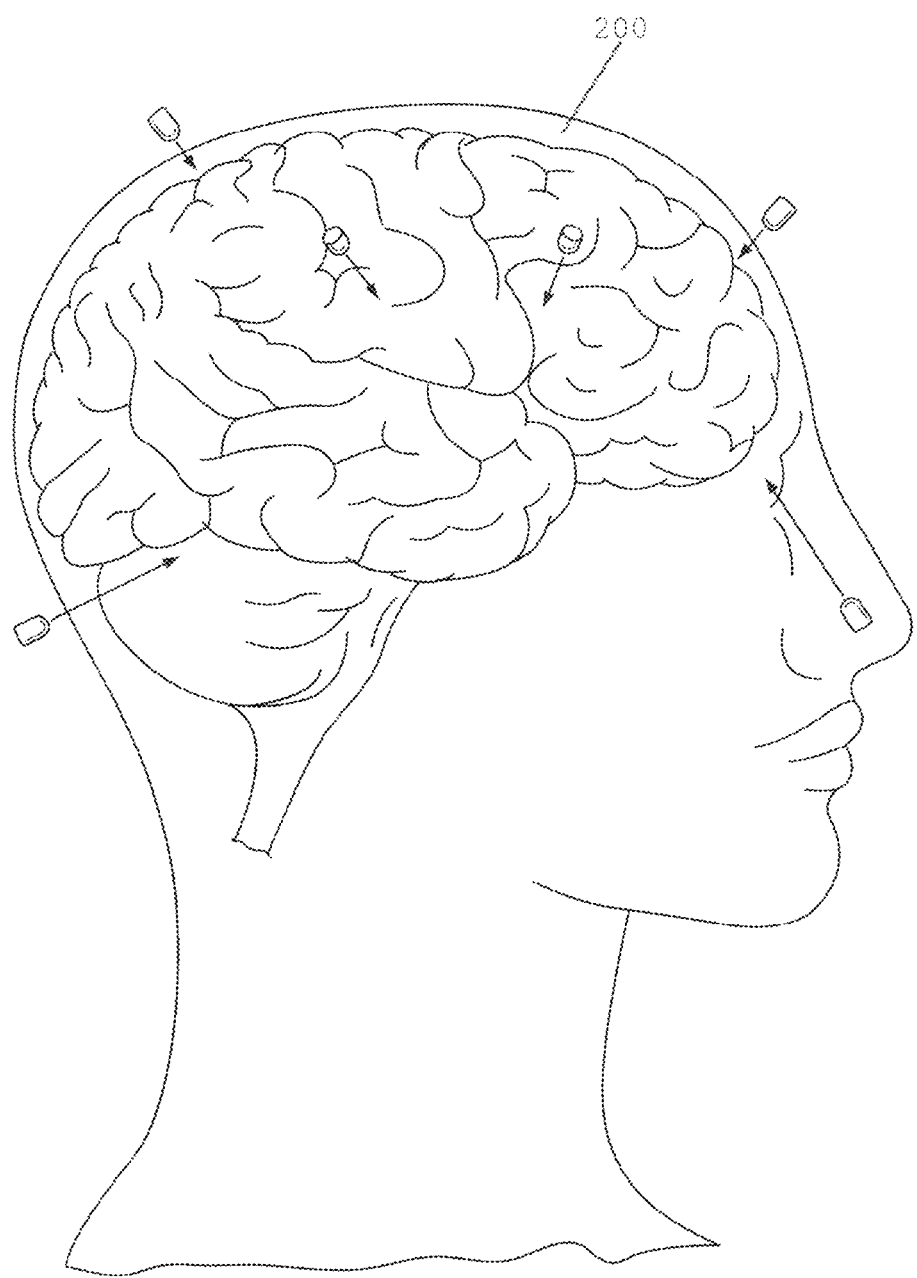
FIG. 5 is a side view of the light generating units of a preferred embodiment of the system of the present invention directed to areas of the brain of a subject.

As shown in FIGS. 2 to 4, the present invention provides a preferred embodiment of an apparatus 100 which combines a transcranial light therapy headset 102, a secondary light therapy headset 104 and an intranasal light therapy unit 106. The portable controller assembly 108 can serve as a central processing unit for the transcranial headset 102, secondary headset 104 and intranasal unit 106.

Figure 6:
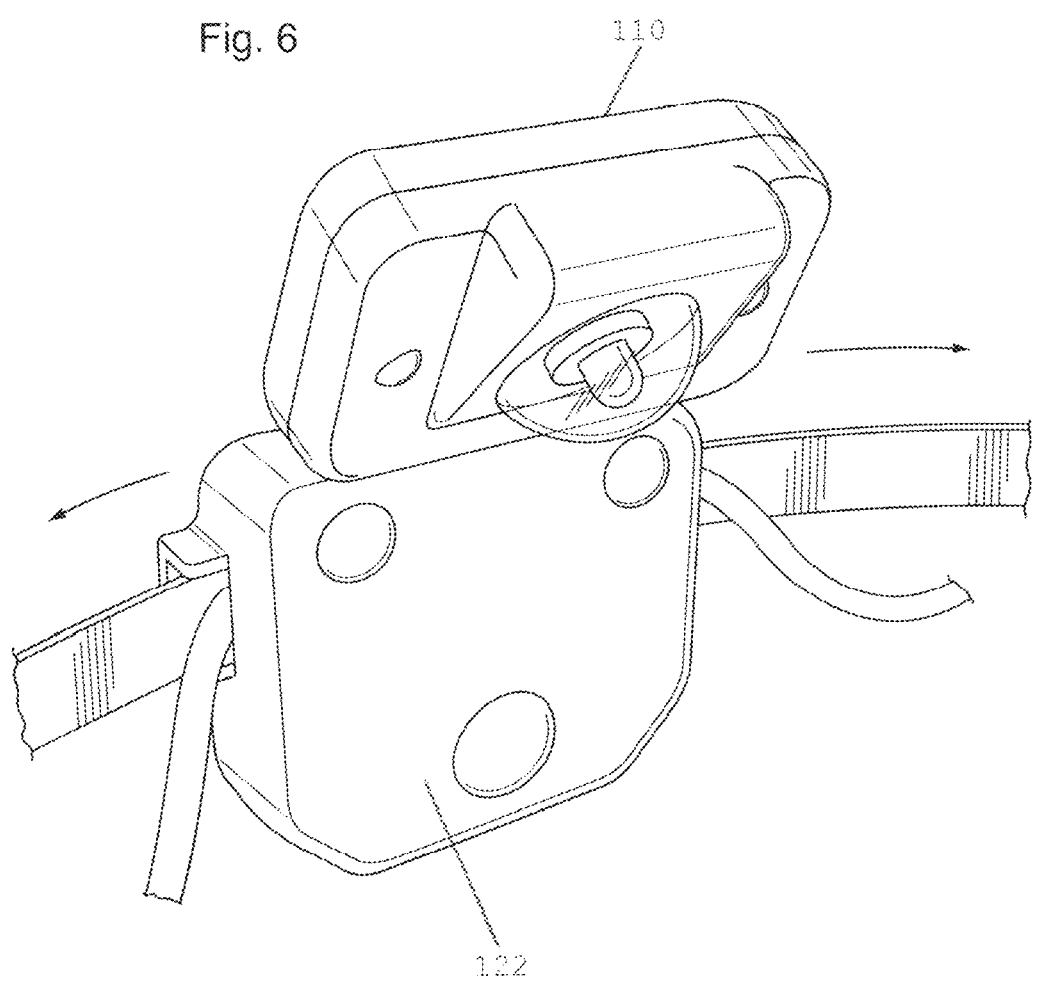
FIG. 6 is an isolated view of a configured irradiation unit of the transcranial photobiomodulation (PBM) headset of FIG. 2.
Figure 8:
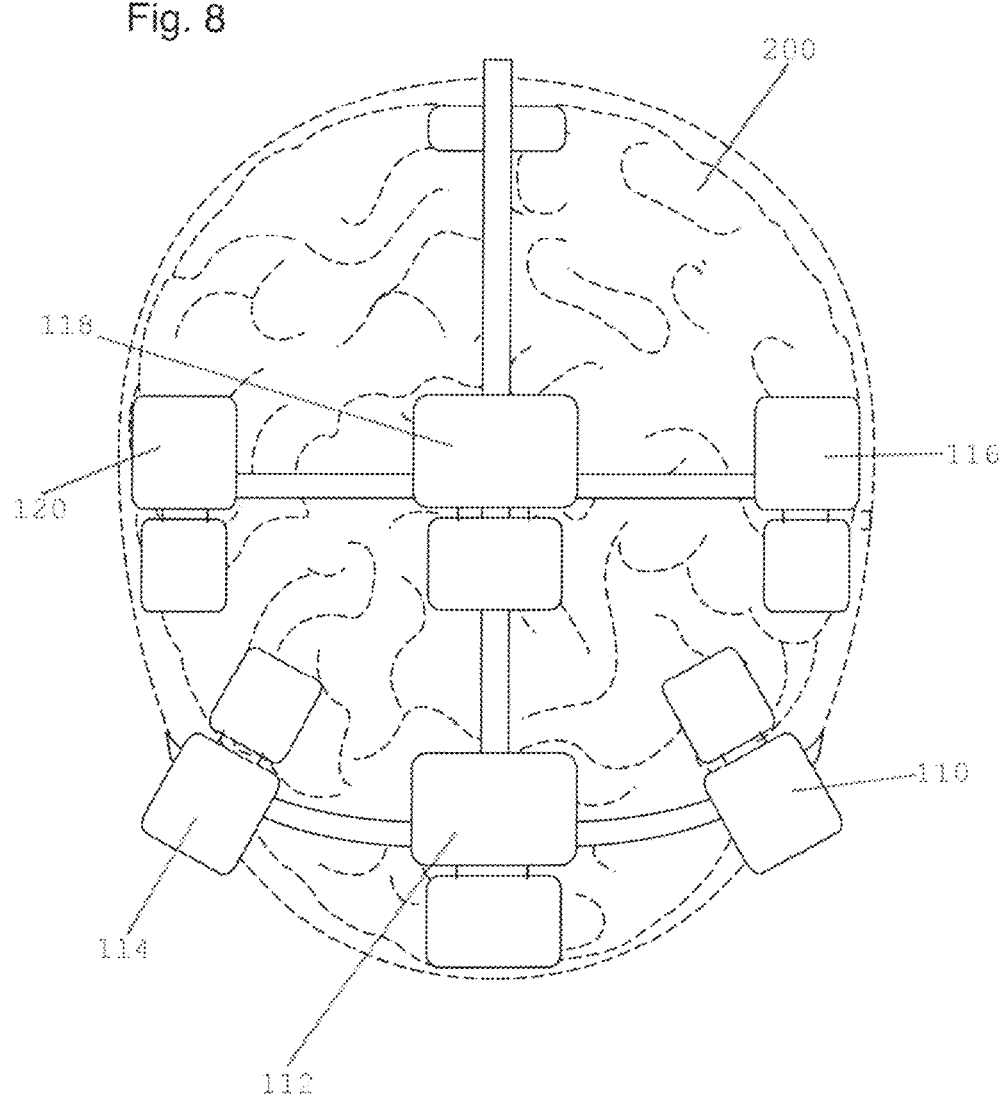
FIG. 8 is a top view of the photobiomodulation (PBM) headset and secondary PBM headset of FIG. 2 applied to a subject.

The headset 102 comprises one or more configured irradiation units 110, 112, 114, 116, 118 and 120, which may be placed as shown in FIG. 8. As can be seen in FIG. 6, each of the configured irradiation units 110, 112, 114, 116, 118 and 120 includes a portable hollow casing having fixed dimensions, a sized internal spatial volume, and an external surface configuration suitable for application to the skull 200. The portable hollow casing comprises a light energy transmitting material which forms at least a portion of the configured external surface for said hollow casing. At least one light generating unit is entirely housed and contained within said internal spatial volume of said hollow casing and is capable of generating light energy sufficient to penetrate through the skull and to pass into the brain. Each of the configured irradiation units 110, 112, 114, 116, 118 and 120 also has a driver circuit 122 which is in communication with the controller assembly 106 and controls the light generating unit(s).

A frame 124 is provided in the headset 102 to support the configured irradiation units 110, 112, 114, 116, 118 and 120 and to adapt the headset 102 for at will placement of the light transmitting external surface of the configured irradiation units 110, 112, 114, 116, 118 and 120 at a fixed position and desired irradiation direction on the skull 200. Each of the configured irradiation units 110, 112, 114, 116, 118 and 120 can be moved by sliding along the frame 124. In this manner, the configured irradiation units 110, 112, 114, 116, 118 and 120 can be set at many different locations on the skull 200 to target many different locations in the brain. Support pads 126 are preferably provided to help secure the headset 102 to the skull 200 and to make the headset 102 more comfortable for the patient to wear.

In the preferred embodiment shown in FIGS. 2 to 4 and 8, the frame 124 supports six configured irradiation units 110, 112, 114, 116, 118 and 120, and each configured irradiation unit 110, 112, 114, 116, 118 and 120 has at least one light generating unit(s) each. The six units are positioned in the headset 102 such that they target specific areas of the brain. In the preferred embodiment shown in FIGS. 2 to 5 and 8, the units are positioned to target the following parts of the brain:

(i) right lateral parietal cortex (LPC) and/or posterior cingulate cortex (PCC);
(ii) precuneus (PCu);
(iii) left lateral parietal cortex (LPC) and/or posterior cingulate cortex (PCC);
(iv) right dorsal-lateral prefrontal cortex (DLPC);
(v) dorsal medial prefrontal cortex (dmPFC); and
(vi) left dorsal-lateral prefrontal cortex (DLPC).

Figure 7:
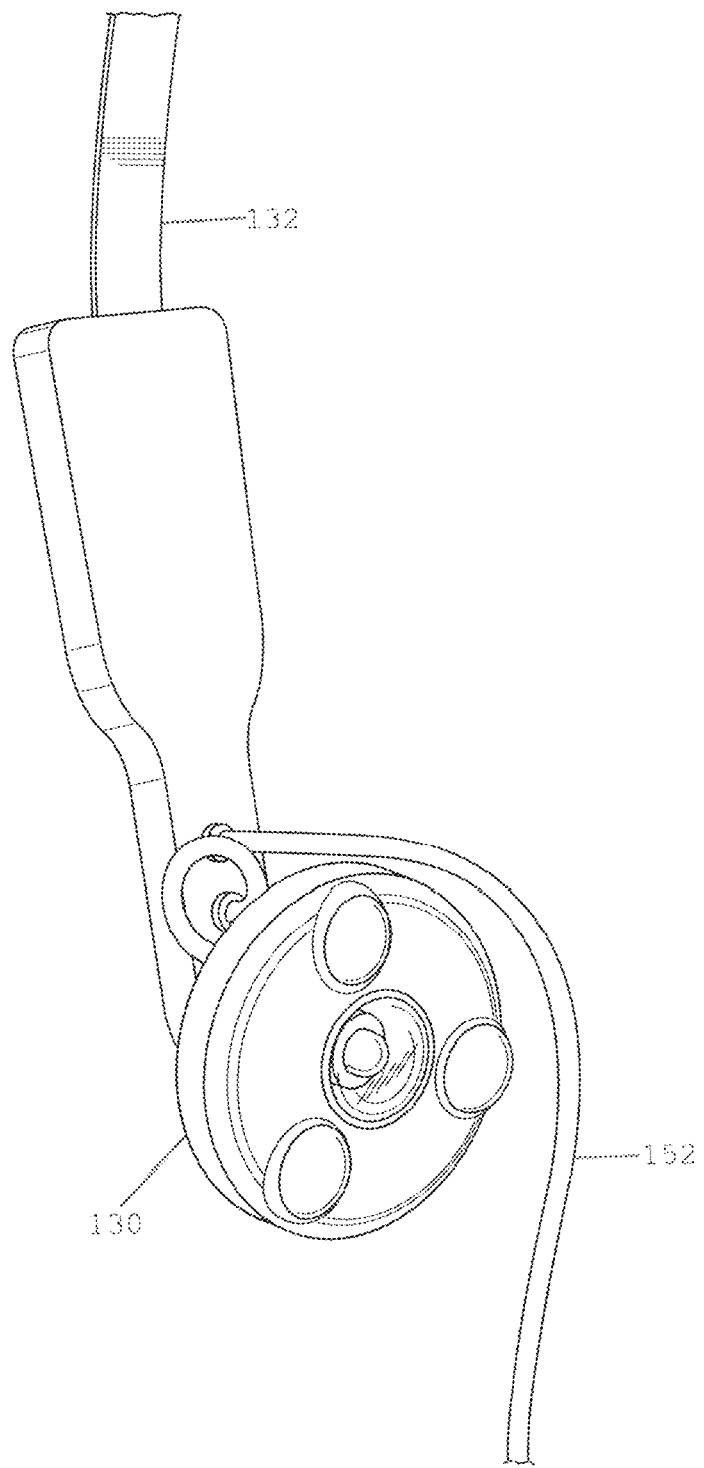
FIG. 7 is an isolated view of a configured irradiation unit of the secondary photobiomodulation (PBM) headset of FIG. 2.

The secondary headset 104, which can be seen in FIGS. 2 to 4, comprises an additional configured irradiation unit 130. As shown in FIG. 7, configured irradiation unit 130 also includes a portable hollow casing having fixed dimensions, a sized internal spatial volume, and an external surface configuration suitable for application to the skull 200. The portable casing comprises a light energy transmitting material which forms at least a portion of the configured external surface for said hollow casing. At least one light generating unit is entirely housed and contained within said internal spatial volume of said hollow casing and is capable of generating light energy sufficient to penetrate through the skull and to pass into the brain.

A secondary frame 132 is provided in secondary headset 104 to support configured irradiation unit 130 and to adapt the headset 104 for placement of the light transmitting external surface of the configured irradiation unit 130 at a fixed position and desired irradiation direction on the sub-occipital area of the skull 200. Support pads 134 are preferably provided to help secure the secondary headset 104 to the skull 200 and to make the headset 104 more comfortable for the patient to wear.

In the preferred embodiment shown in FIGS. 2 to 5, configured irradiation unit 130 is positioned in the secondary headset 104 on the sub-occipital area such that it targets the cerebellum and/or brain stem.

As can be seen in FIGS. 2 to 4, the intranasal light therapy unit 106 includes a nose clip 140. The nose clip 140 is "L-shaped", and holds a configured irradiation lens 142 inside one of the nostrils of the subject. The configured irradiation lens 142 includes a portable hollow casing having fixed dimensions, a sized internal spatial volume, and an external surface configuration suitable for application to the interior of the nostrils. The portable casing comprises a light energy transmitting material which forms at least a portion of the configured external surface for said hollow casing. At least one light generating unit is entirely housed and contained within said internal spatial volume of said hollow casing and is capable of generating light energy sufficient to penetrate through the nasal tissues and to pass into the brain. The intranasal light therapy unit 104 targets areas of the ventral or underside of the brain such as the ventral medial prefrontal cortex (vmPFC), directly and indirectly via the olfactory bulb to the entorhinal cortex (EC) and parahippocampal area (including the hippocampus).

A first connector 150 is in electrical communication with the configured irradiation units 110, 112, 114, 116, 118 and 120 of the transcranial headset 102, via the driver circuits 122. A second connector 152 is in electrical communication with the configured irradiation unit 130 of the secondary headset 104. A third connector 154 is in electrical communication with the configured irradiation lens 142 of the intranasal light therapy unit 106. This allows for on-demand conveyance of direct electrical current from the portable controller assembly 108 to the light generating units in the configured irradiation units 110, 112, 114, 116, 118 and 120 of the transcranial headset 102, the light generating unit(s) in the configured irradiation lens 130 of the secondary headset 104, and the light generating unit(s) in configured irradiation lens 142 in the intranasal light therapy unit 106.

A portable power bank 160 provides electrical current to the apparatus 100. The power bank 160 can be a standard power bank comprising an encased battery with a circuit to control power flow. Preferably, the power bank 160 is rechargeable by plugging it into an electrical grid via a cable, such that the power bank 160 draws in and stores electrical energy. Alternatively, the power bank 160 may be recharged by other means, such as using photovoltaic panels which charge the internal battery with solar energy. A fourth connector 162 provides electrical communication between the power bank 160 and the controller assembly 108. As such, the power bank 160 provides electrical current to the controller assembly 108, which in turn provides electrical current to the light generating units of the apparatus 100.

Figure 9:
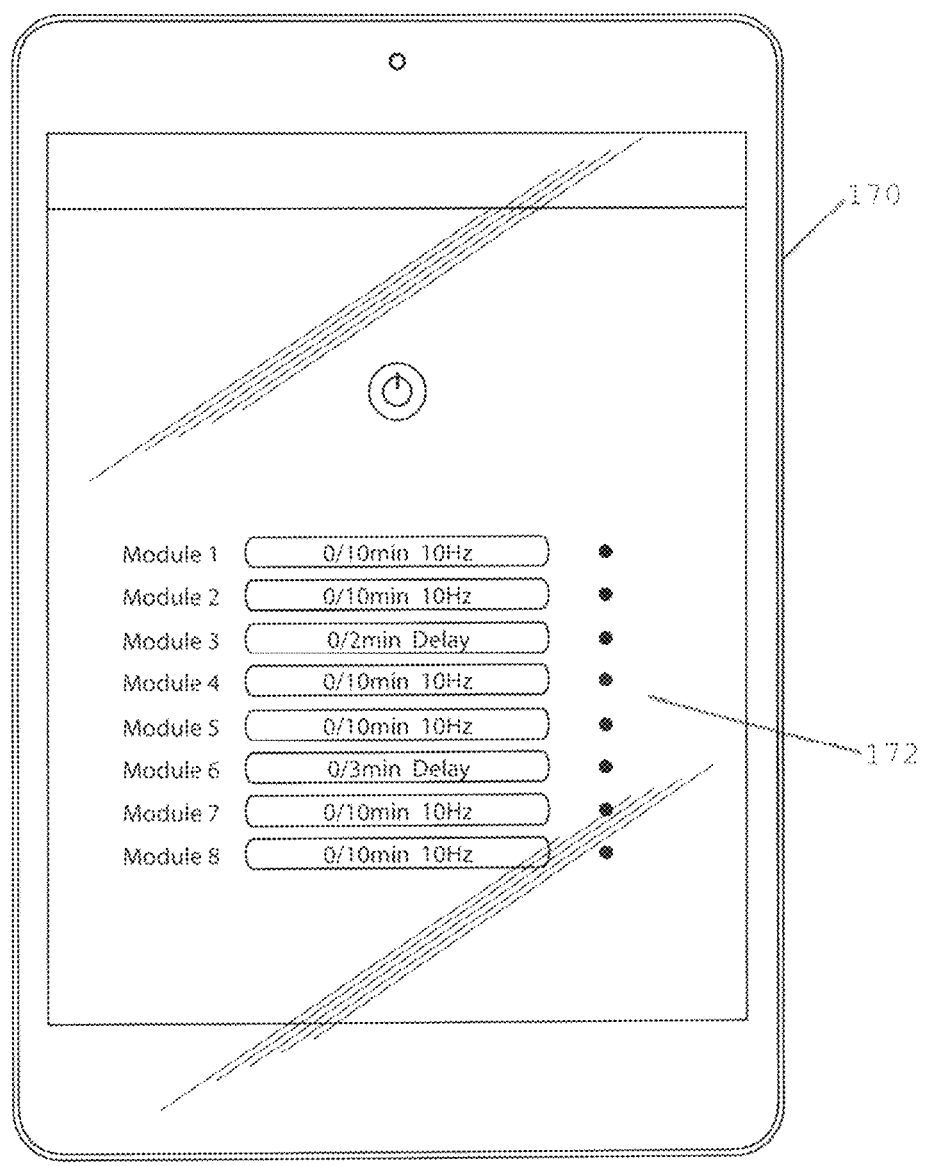
FIG. 9 is an isolated view of the tablet computer of FIG. 2.

A tablet computer 170, shown in FIGS. 2 and 9, provides a system interface 172 for the apparatus 100. The tablet computer 170 has downloaded thereon a PBM parameter-setting computer application which can: (i) turn the controller assembly on and off; and/or (ii) adjust the light energy parameters of each individual light generating unit, including but not limited to wavelength, coherency/synchrony, energy (as measured in Joules (J)), Power (as measured in Watts (W) or milliwatts (mW)), irradiance (W/cm$^2$), radiant exposure or dose or fluence density (J/cm$^2$), exposure time (seconds), wave type (continuous or pulse), duty cycle (percentage), fraction protocol (number of patient treatment sessions), light beam size (area of landed beam), and light beam penetration (delivery) distance. Preferably, each of the configured irradiation units 110, 112, 114, 116, 118, 120 and 130 and the configured irradiation lens 142 can be selectively switched on and off, as each has its own light generating unit and its own driver circuit 122. In alternative embodiments, the tablet computer 170 may be replaced by a smart phone, smart watch, laptop computer or desktop computer.

Furthermore, the tablet computer 170 serves as a system interface 172 where a user selects icons on the touch screen to turn the controller assembly 108 on and off and/or adjust the light energy parameters of each individual light generating unit. Once the user inputs instructions into the system interface 172, instructions are transmitted to the controller assembly 108 which then adjusts the parameters of the light energy being delivered to by the light generating units. In this embodiment, the tablet computer 170 is linked to and communicates with the controller assembly 108 by wireless means. However, any appropriate wired or wireless communications via protocols such as BLUETOOTH™, Wi-Fi, Near Field Communications (NFC), Radio Frequency Identification (RFID), 3G, Long Term Evolution (LTE), Universal Serial Bus (USB) and other protocols and technologies known to those skilled in the art can be used to link the tablet computer 170 to the controller assembly 108.

FIG. 1 illustrates an EEG device 1000 which can be preferably be used as a part of the system and apparatus of the present invention. The EEG device 1000 comprises a cap 1010 that contains one or more electrodes 1012 for reading and recording a subject's electrical brain activity. The embodiment shown in FIG. 1 has 19 electrodes 1012. However, EEG devices vary widely regarding the number of electrodes, with 32 and 64 electrodes also being common configurations, and 128 and 256 electrodes used in research. The electrodes 1012 are connected to and send data on the subject's electrical brain activity to the tablet computer 170

(or alternatively, another computing device) having EEG analysis software downloaded thereon.

Preferred Methods of Therapeutic Treatment of the Present Invention:

The system and apparatus described above can be used in preferred methods of the present invention. In preferred methods, light energy is preferably delivered to targeted areas of the brain, such as the cortical hubs of the DMN. As mentioned above, lesions in these cortical hubs are associated with many brain disorders, such as Alzheimer's disease and dementia. The effective delivery of light to these damaged areas aims to stimulate healing, with the pulsing of preferably 40 Hz to modify microglia into the non-inflammatory phenotype to enhance its efficacy. At the cellular level, the photoacceptor respiratory enzyme cytochrome oxidase is particularly sensitive to light in the visible red region and near-infrared region of the light spectrum, and converts the absorbed light of these red and near-infrared wavelengths into cellular energy molecules of adenosine triphosphate (ATP). There is a resulting increase in ATP synthesis and oxygen consumption, thus improving mitochondrial metabolism in-vivo. This preferably promotes growth and healing of the neuronal cells and aims to improve the condition of the brain disorder through the process of gene transcription.

The method for performing non-invasive irradiation light therapy in order to achieve brain neurostimulation in a living mammalian subject preferably comprises the following steps and actions:

Step 1: Obtaining a light energy-emitting apparatus 100 of the present invention.

Step 2: Placing a transparent external surface of one or more of the configured irradiation units 110, 112, 114, 116, 118, 120 and 130 at a desired fixed position adjacent to the skull 200 of a subject such that light energy emitted by said configured irradiation units 110, 112, 114, 116, 118, 120 and 130 will penetrate through the subject's skull 200 and pass into at least one portion of the brain in-vivo; and placing a transparent external surface of a configured irradiation lens 142 within a nostril at a desired fixed position adjacent to the internal lining of a subject's nasal cavity such that light energy emitted by said configured irradiation lens 142 will penetrate through the subject's nasal tissues and pass into at least one portion of the brain in-vivo.

Step 3: Causing the light generating units of said positioned configured irradiation units 110, 112, 114, 116, 118, 120 and 130 to generate light energy having parameters sufficient to penetrate through the subject's skull 200 and to pass into the brain; and causing the light generating units of said positioned configured irradiation lens 142 to generate light energy having parameters sufficient to penetrate through the subject's nasal tissues and to pass into the brain.

In one preferred embodiment, the irradiation units 110, 112, 114, 116, 118, 120, 130 and 142 are positioned to target the following: (i) right lateral parietal cortex (LPC) and/or posterior cingulate cortex (PCC); (ii) precuneus (PCu); (iii) left lateral parietal cortex (LPC) and/or posterior cingulate cortex (PCC); (iv) right dorsal-lateral prefrontal cortex (DLPC); (v) dorsal prefrontal cortex (PFC); (vi) left dorsal-lateral prefrontal cortex (DLPC); (vii) via the nasal cavity, the ventral medial prefrontal cortex (vmPFC), entorhinal cortex (EC) and/or parahippocampal area (including hippocampus); and (viii) cerebellum and/or brain stem.

As mentioned above, the system, apparatus and method of the present invention may also comprise a tool for diagnosing abnormal brain function. The diagnostic tool may be, for example, a functional magnetic resonance imaging (fMRI) device, a functional Near-Infrared Spectroscopy (fNIRS) device, a Magnetoencephalography (MEG) device or an Electroencephalography (EEG) device.

The following is a description of a preferred embodiment of the method of the present invention which uses an EEG device as diagnostic tool.

1. An EEG device 1000, such as an EEG cap 1010 with one or more electrodes 1012, is placed on the skull 200 of a subject. Brain waves at various oscillations in the subject are detected.

2. Data regarding the subject's brain waves is transmitted to a tablet computer 170 (or alternatively, another computing device) with EEG analysis software downloaded thereon. The subject's brain wave data is analyzed. In particular, the subject's brain wave properties are compared to normal brain wave properties, and analysis data of the subject's brain activity is produced. If present, abnormal brain wave properties are detected and preferably also identified with specific areas of the brain.

3. The analysis data of the subject's brain activity, including any abnormal brain wave data, is transmitted to or retrieved by a PBM parameter-setting software application, preferably downloaded on the same tablet computer 170. Based on the analysis data, the PBM parameter-setting software application selects appropriate light energy parameters with respect to one or more of wavelength, coherency/synchrony, energy (Joules (J)), Power (Watts (W) or milliwatts (mW)) or irradiance (W/cm$^2$), radiant exposure (J/cm$^2$), exposure time (seconds), wave type (continuous or pulse), frequency (Hertz (Hz)), duty cycle (percentage), fraction protocol (number of patient treatment sessions), light beam size (area of landed beam), and light beam penetration (delivery) distance for each configured irradiation unit 110, 112, 114, 116, 118, 120 and 130 and configured irradiation lens 142.

4. Instructions regarding the appropriate light energy with specifically selected parameters is transmitted from the tablet computer 170 to the controller assembly 108.

5. The controller assembly 108 causes the light energy with specifically selected parameters to be directed to the subject using one or more irradiation units that are strategically positioned on the subject's scalp, neck, nose, eyes, ears or any other part of the subject's body. In one preferred embodiment, the irradiation units are positioned to target the following: (i) right lateral parietal cortex (LPC) and/or posterior cingulate cortex (PCC); (ii) precuneus (PCu); (iii) left lateral parietal cortex (LPC) and/or posterior cingulate cortex (PCC); (iv) right dorsal-lateral prefrontal cortex (DLPC); (v) dorsal medial prefrontal cortex (dmPFC); (vi) left dorsal-lateral prefrontal cortex (DLPC); (vii) via the nasal cavity, the ventral medial prefrontal cortex (vmPFC), entorhinal cortex (EC) and/or parahippocampal area (including hippocampus); and (viii) cerebellum and/or brain stem. One or more irradiation units can be added to target locations such as the vagus nerves on the neck, the ear lobe/canal and the eyes (preferably positioned inside an eye goggle), the gut or any other parts of the body.

Combining PBM Intervention with Diagnostics for Endogenous Brain Connectivity, Coherency and Synchrony:

Dysfunctional brain networks are often associated with aberrant connectivity, coherency or synchrony in their brain wave patterns. Degenerative conditions and hypoactivity are associated with the lack of these properties or have persistent hyper-coherency/synchrony in the slower oscillations in delta and theta. These could be indicated with EEG readings.

Re-establishing normative oscillation power across the networks may alleviate symptoms of neurodegeneration or other psychiatric conditions such as attention deficit hyperactivity disorder (ADHD) and bipolar disorder. It could be applicable for more precise locations. For example, EEG diagnostics could indicate hyper-coherency that could be "locked-in" in theta oscillations between the F3 and F4 or other locations (in accordance with the 10-20 EEG system) which could be broken up by invoking pulse frequency that are out-of-phase with the endogenous theta oscillation. Likewise, for hypo-coherency between two locations, added power into oscillations that are in-phase with the endogenous oscillations could strengthen the connectivity. Using PBM intervention coupled with a diagnostics method like EEG to achieve this is novel and useful. A version of this selective intervention method may be used to achieve enhanced performance of a normal brain or an altered mental state.

In one preferred embodiment, the method of the present invention uses an EEG device to detect whether the neural oscillations between two different locations in a subject's brain are coherent (in-phase or synchronous) or non-coherent (out of phase or asynchronous) with each other. They may also indicate the level of connectivity. Abnormal coherency may be indicative of a neural condition. For example, in ADHD of the inattentive subtype, the frontal lobes or some areas of the brain could be locked in hyper-coherency and high power in the low oscillations of delta and theta, which may be corrected by invoking out-of-phase oscillations in these areas. Coherency/synchrony data may be used to select operational parameters for treatment using the system and apparatus of the present invention. As many conditions present aberrant coherency/synchrony, including Alzheimer's disease, pulsed PBM could be a tool that is used to correct the aberrations, and hence the symptoms. Real time EEG readings could intelligently call for PBM of selected oscillations for selected brain locations in specific time series that would either be out-of-phase with the endogenous brain oscillations to interrupt hyper-coherency or in-phase to strengthen coherency.

In preferred embodiments where the method of the present invention is using a functional Near-Infrared Spectrscopy (fNIRS) device or functional magnetic resonance imaging (fMRI), data regarding blood oxygenation in the brain is collected. Such collected data is analyzed, preferably by comparison with normal blood oxygenation data, and determined as being normal or abnormal. Based on this data analysis, the appropriate light energy is selected with specific parameters with respect to one or more of wavelength, coherency/synchrony, energy (Joules (J)), Power (Watts (W) or milliwatts (mW)) or irradiance (W/cm$^2$), radiant exposure (J/cm$^2$), exposure time (seconds), wave type (continuous or pulse), frequency (Hertz (Hz)), duty cycle (percentage), fraction protocol (number of patient treatment sessions), light beam spot (area of landed beam), and light beam penetration (delivery) distance. Instructions regarding the appropriate light energy with specifically selected parameters is sent to the controller assembly. The controller assembly causes the light energy with specifically selected parameters to be directed to the subject using one or more irradiation units that are strategically positioned on the subject's scalp, neck, nose, eyes, ears or any other part of the subject's body.

System/Apparatus/Method Parameters and Dosimetry:

An effective and safe system and method in compliance with the present invention provides choices and control over a wide range of operational parameters. These operational parameters include but are not limited to the choice(s) of: the light wavelength, coherency/synchrony, energy (Joules (J)), Power (Watts (W) or milliwatts (mW)) or irradiance (W/cm$^2$), radiant exposure (J/cm$^2$), exposure time (seconds), wave type (continuous or pulse), frequency (Hertz (Hz)), duty cycle (percentage), fraction protocol (number of patient treatment sessions), light beam spot (area of landed beam), and light beam penetration (delivery) distance.

1. Choice of Therapeutic Wavelengths

The wavelengths shown to be most effective at inducing in vivo beneficial effects in living neural cells have generally been in the optical window of the red and near-infrared red range (NIR) of the spectrum (i.e., between 620 nm and 1400 nm wavelengths). Successful treatments for brain irradiation have typically been performed at 633-670 nm wavelengths or 808-1072 nm (near-infrared) wavelengths in both animals and humans. Accordingly, any light wavelength ranging between about 620-700 nm and 780-1400 nm is deemed to be acceptable for therapeutic use with the present invention.

In general however, the longer the wavelength of light, the lower the energy required for successful treatment and it is well established that the longer the light wavelength, the deeper the penetration distance of the light passing into and through living tissues. However, in live mammalian tissues, wavelengths longer than 850 nm are increasingly and exponentially absorbed by water in the body. Penetration of light energy through living tissues depends not only on the chosen wavelength but also on the optical properties of the targeted tissues. For live mammalian brains, the maximal penetration distance of light energy within the gray and white matter of the brain occurs at wavelengths between about 620 nm-1400 nm in the NIR light region. For this reason also, the NIR light wavelengths between about 620 nm-1400 nm are generally preferred for use, and for penetration and nervous tissue response, around 810 nm is particularly preferred.

2. Continuous Wave (CW) Vs Pulse Frequency

Generally, in PBM, pulsing has been used to cool high powered lasers under the assumption that high power allows for deeper penetration without creating undesired heat. The principle also applies to LEDs. It could activate more cellular energy (ATP), as demonstrated in a study on rabbits. The other mechanism of action hypothetically involves the first part of a pulse containing photons to take all chromophore molecules in the upper tissue layer to excited states, opening the way for more photons into the tissue during the next pulse. In an animal study, researchers testing with 810 nm laser found that pulsing at 10 Hz produced greater recovery from traumatic brain injury than 100 Hz. They suggested that the antidepressant activity of the light therapy was a contributing factor.

Pulsing visible light has the risk of triggering a seizure episode. The present invention preferably seeks to pulse only invisible near infrared light to avoid this problem. In addition, a seizure is only triggered in photic visual processing, that is, the light has to be seen by the eyes and processed in the visual cortex. If light in a visible wavelength is used in the present invention, it may be preferable to avoid using a pulsing mode on humans due to a possible risk of photosensitive epilepsy events. For this reason, it may be preferable to use pulsing invisible near infrared light, such as light having a wavelength of about 810 nm, in the present invention. Furthermore, the direction of light through the scalp and nasal cavity reduces the risk of photosensitive epilepsy.

3. Pulse Frequency

An alpha pulse frequency is preferred for treatment of traumatic brain injury (TBI), preferably about 10 Hz. An alpha pulse frequency is also preferred from the treatment of other conditions such as depression, anxiety, hypoxia and stroke, preferably about 10 Hz.

Alzheimer's disease (AD) often present reduced or aberrant processing or encoding of short-term and episodic memory. Studies have found that memory encoding is dysfunctional, expressing excitotoxicity without the presence of gamma oscillation which seems to have a neutralizing inhibitory effect. This can be invoked with PBM at 40 Hz. In addition, investigations reveal that light at gamma oscillation at 40 Hz also modifies microglia (which has the role of removing AD-related protein plaques) into the non-inflammatory type that is useful and safe to address AD pathology. The invention can direct PBM at 40 Hz intervention to the lesions where the plaques are accumulated to help remove and prevent further accumulation. This pulsing feature substantially adds to the theory that PBM with the pulse rate can enhance neuronal healing.

A gamma pulse frequency is preferred for treatment of AD, preferably about 40 Hz. Furthermore, a gamma pulse frequency is preferred for treatment of Parkinson's Disease, preferably about 40 Hz, as this tends to activate non-inflammatory phagocytic microglia cells which are able to engulf foreign materials in the brain. In addition, a gamma pulse frequency is preferred for treatment of other conditions such as attention deficit hyperactivity disorder (ADHD), autism and schizophrenia where endogenous gamma oscillations are typically low.

The inventor and his collaborators performed recent tests using the delivery of 810 nm light at pulse frequency of 40 Hz from LEDs. It has been previously observed that aberrant increases in network excitability and compensatory inhibitory mechanisms in the hippocampus may contribute to Aβ-induced neurological deficits in mouse models. EEG recordings in mouse models indicated network hypersynchrony, primarily during reduced gamma oscillatory activity. Restoring gamma oscillation may inhibit overactive synaptic activity and reduce hypersynchrony, memory deficits, and premature mortality—conditions associated with AD. In individuals with AD, this phenomenon is associated with a risk for an increased formation of Aβ protein associated with AD. The gamma pulse frequency of 40 Hz has been demonstrated to attenuate Aβ proteins production in the visual cortex of mice that were in environments illuminated with light pulsing at that rate. It has been theorized that the 40 Hz pulse rate modify microglia into the non-inflammatory state that engulfs the unwanted Aβ protein deposits. When 40 Hz pulsing light were optogenetically induced in the hippocampus, Aβ peptide levels in the location also attenuated significantly. From the data, Aβ may be attenuated in the brain regions that process pulsed light at 40 Hz, and if light pulsed at 40 Hz is directed to the right areas associated with the DMN, it could be an impactful treatment for AD.

The system and apparatus of the present invention can also be used for non-medical treatments, such as to generally improve cognition, athletic performance and meditation. In such cases, the pulse frequency is an important parameter.

Regarding the general improvement of a subject's cognitive abilities, including the ability to acquire knowledge and understand it through thought, experience and the senses, a beta and/or gamma pulse frequency is preferred, and preferably at about 40 Hz.

With respect to improvement of athletic performance, an alpha pulse frequency is preferred for those situations requiring the athlete to focus and calmly think through or perform a mental task, preferably about 10 Hz. A gamma pulse frequency is preferred for those situations requiring the athlete to make quick decisions under time pressure, preferably about 40 Hz.

Meditation is a practice where a person achieves a mentally clear and emotionally calm state. Reaching a high-level meditative state can take hours even for long term meditators. For a long-term meditator, a gamma or a higher pulse frequency is preferred to help them reach a high-level meditative state more quickly (typically in a matter of less than 5 minutes), preferably from about 40 Hz or more, preferably at about 80, 120, 200 Hz or higher.

The system and apparatus of the present invention can deliver a pulse frequency ranging from 0 to 1000 Hz or higher which allows for experimentation at many pulse frequencies in between.

4. Choice of Coherent Vs Non-Coherent Radiation (Lasers Vs Non-Laser Light-Emitting Diodes)

Lasers provide coherent electromagnetic radiation that is unidirectional, hence allowing for a more concentrated energy coupled with a high energy input. Modern laser light sources are usually constructed in low intensity semiconductor formats, with divergence that allows for safety. Such laser light sources may have advantages over LEDs, which include: (i) a higher degree of tissue penetration; (ii) an efficient optic coupling; and (iii) a high monochromaticity. When a deeper penetration distance of living tissues is required, given the same parameters of wavelength, energy dosage and intensity, the coherent light of lasers may be preferable to the non-coherent light generated by light-emitting diodes (LEDs).

However, for many therapeutic applications, light coherency as such is not required for clinical efficacy, and in those medical circumstances where a greater distance of tissue penetration is needed, it is often deemed better met using non-coherent light at longer wavelengths from light-emitting diodes (LEDs). In recent years, light-emitting diodes (LEDs) have become viable therapeutic alternatives to lasers as light sources. It is postulated that the cell's photoacceptors (particularly cytochrome oxidase) do not discern between the coherency or non-coherency of the light photons that are received. In any event, light scatters when inside tissues. Therefore, given the same wavelength of light, the energy dosage and intensity input received at the cell's photoacceptor receptors using light-emitting diodes (LEDs) will yield therapeutic outcomes which are similar or identical to that provided by coherent light of laser light sources. Although penetration with LED non-coherent light is typically shallower, the LED generated non-coherent light has the advantage of providing a wider area of landed beam spot coverage.

The system, apparatus and method of the present invention recognizes the coherent vs. non-coherent differences existing between light from laser sources and light-emitting diode sources, and provides for both possibilities by carefully choosing between them on the basis of the optimum condition for particular application purposes (i.e., the particular disease state or disorder to be therapeutically treated will dictate which is the better format).

Therefore as a first illustrative example, when there is an advantage in irradiating only one specified area in the mid-brain area, such as irradiating the more deeply located pineal gland and suprachiasmatic nucleus (SCN) in order to restore normal circadian rhythms and correct sleep disorders, the coherent light of the laser light source may be preferred for its greater tissue penetration distance. As a meaningful alternative however, the use of non-coherent LED light at a longer wavelength (preferably in the NIR range) in combination with a longer treatment time may adequately compensate for the loss of maximal tissue penetration distance that can be provided by the coherent light of the laser source. However, compared to lasers, LEDs do not have the risk of damaging the eye retina.

As a second illustrative example in favor of non-laser LEDs, although the coherent light from a NIR 810 nm laser source may have been favored because of its deeper tissue penetration capabilities, its invisible property has greater risk. The 810 nm laser light is invisible to the human eye. Thus, whereas a visible laser would have triggered eye blinking as an autonomic defense mechanism, an invisible laser does not. There is therefore substantial risk of inadvertently causing retinal injury to the eye if he or she looks directly at the laser light source for a prolonged period. This is the reason for regulatory restrictions on the use of lasers. Hence the present invention which offers a non-laser LED is safer, and removes the safety risk when used unsupervised at home, without the regulatory restrictions. This does not exclude the use of NIR lasers in clinical or research settings. Under the same argument, low powered visible red lasers are relatively safe when compared to invisible lasers.

Another advantageous aspect of non-coherent LED generated light is that the use of such non-coherent light creates relatively lower heat in comparison to laser generated light. This may allow the living brain tissue to be exposed to non-coherent LED generated light for longer periods of time using wavelengths at relatively low power densities, which in turn allows the time for more efficacious modulation of neural activities. Thus, if the treatment time is to be prolonged for medical efficacy, as exemplified by the treatment of traumatic brain injury, non-coherent LED generated light wavelengths at relatively low power densities are preferred over the use of laser generated light in order to avoid the risk of causing undesired thermal injury to the brain tissue.

For general therapeutic use purposes therefore, the present invention may preferably use NIR LED light sources and non-coherent light wavelengths for brain therapy treatments as well as for preventive medicine applications. This preference generally includes and encompasses those medical/clinical/pathological conditions relating to human cognitive functions, neurodegeneration, vascular dementia, migraine, pain, and human memory deficits. It also includes non-medical uses that include cognitive enhancement and altered states.

5. Therapeutic Energy and Other Parameters

Light energy is traditionally measured as Joules (J)=Power (W)×Time (seconds). For brain stimulation purposes, very little light energy is required to stimulate mitochondrial activity. One reference point for medical efficacy in use today is the time-tested intravenous light irradiation technique involving light being directly injected into the vein (used mainly in Russia, Germany and many other countries around the world for decades but not Food and Drug Administration (FDA) approved for United States), and which normally follow the parameters of lasers with a wavelength of 632.8 nm, a power of about 1.5 mw (or another very low number), and a time of about 30 minutes per treatment session. On this basis, in a common protocol, patients are usually treated once a day for the first three calendar days, and then treated once every two calendar days, until a total of ten patient treatment sessions is reached. For each patient treatment session, light energy of about 2.7 Joules (1.5/1000 W×30 minutes×60 seconds) is delivered.

In vitro studies have shown that 1-3 J of energy with visible red light is sufficient to activate PBM mechanisms for cellular recovery in cells on a petri dish. In the present invention, much higher power (resulting in higher dose energy) is preferably factored in to account for the penetration through layers of tissues.

Telemetry:

In a further aspect, the system and method of the present invention uses telemetry to record and monitor data relating to the treatment of the subject. For example, the system and apparatus of the present invention is used to treat the subject and acts as a telemeter. Data regarding whether the system is on or off, and the operational parameters used by the system and apparatus of the present invention, including but not limited to wavelength, coherency/synchrony, energy (Joules (J)), Power (Watts (W) or milliwatts (mW)) or irradiance (W/cm$^2$), radiant exposure (J/cm$^2$), exposure time (seconds), wave type (continuous or pulse), frequency (Hertz (Hz)), duty cycle (percentage) fraction protocol (number of patient treatment sessions), light beam size (area of landed beam), and light beam penetration (delivery) distance, is transmitted to a base. At the base, the data is recorded and can be monitored.

The data may be transmitted from the telemeter to the base by wireless transfer mechanisms including but not limited to radio, ultrasonic or infrared systems. Alternatively, the data may be transmitted over media including but not limited to telephone networks, computer networks, optical links and other wired communication systems. Alternatively, the network could be connected and updated via a Blockchain technology.

In the field of neurotelemetry, it is known to use an EEG device as a telemeter where the EEG data is collected by the EEG device and transmitted to a base for monitoring. For example, in some cases where any decline in the patient's condition may require immediate assistance, the EEG data may be transmitted to a registered EEG technologist for continuous or intermittent monitoring. In one preferred aspect of the present invention, the system and method comprise of the collection and transmission to a base of both the EEG data and the data regarding the operational parameters used by the system and apparatus of the present invention. In this preferred embodiment, the information from both sets of data can be used to provide enhanced treatment of the patient. For the large part, the parameters of the system at the user end would preferably be adjusted automatically to provide the optimum treatment for a medical condition, with the option for manual overrides.

Combining PBM Intervention with Diagnostics for Auto-Intervention:

Assuming that the brain can fundamentally respond to various PBM parameters, through brain-computer interface (BCI) and based on EEG diagnostics, we could automate the adjustments of PBM parameters so that we can achieve more normative brain patterns. For normal brains, we may possibly enhance mental performance. For example, we recognize that endogenous gamma oscillations are present in successful memory encoding and cognition. By invoking gamma, we may be able to entrain the brain for better quality endogenous gamma oscillations, and hence enhance mental performance.

The state of the art for non-invasive brain stimulation for improved brain functions has been to use some form of electrical stimulation such as transcranial direct current stimulation (tDCS) and transcranial alternating current stimulation (tACS); or magnetic stimulation such as transcranial magnetic stimulation (TMS) or some variations of these methods. The nature of electrical and magnetic stimulation methods involved instruments that inherently have not produced statistically significant changes without uncomfortable side effects. PBM inherently does not have mechanical or thermal effect on the user and yet have demonstrated significant modulation in brain patterns. It is therefore a much more appropriate method for easy stimulation, and superior as a platform to design a system for quick customization of intervention based on say, EEG readings. The design of a system in this invention that would allow for the adjustments of key parameters for customized PBM intervention to achieve desired outcomes is novel and useful. Apart from leading to a tool to resolve many neurological and psychiatric conditions, it may even enhance mental performance. The parameters would involve for each selected light emitting diode (LED), changes in the pulse frequency, power output, pulse, duty cycle. They also include selected LED-to-LED or subnetwork-to-subnetwork pulse coherency/synchrony to achieve oscillating in-phase or out-of-phase with endogenous oscillations.

The usability of the PBM system could be coupled with a computer database for a closed-loop system that could automate the selection and execution of parameters to correct aberrant brain oscillations. The database would grow organically based on user-community sharing of information that continuously updates it. The whole process could be automated. The automation of such a system particularly, the intervention tapping on an organically growing database of normative database is also novel and useful.

In addition, the user end of the system has the option of being tracked remotely in an embedded wireless telemetry system to monitor the use, providing information about whether the device is being used, time used, location and whether it is functioning properly. The connection allows for remote adjustments of the parameters to improve or experiments with the interventions to improve outcomes. Apart from safety reasons and adherence to treatment protocols, the information provides improved understanding that leads to customization of treatments and improvements in treatment outcomes. The availability of this system would also improve the quality of clinical trials where the devices can be used at home. Another area of use is for post-traumatic stress syndrome (PTSD). Veterans with PTSD have a high risk of suicide, so on the assumption that the PBM system is effective in alleviating PTSD symptoms, this telemetry capability could prove invaluable. The system would be particularly useful for veterans living in rural or remote areas where they are far away from medical centers. The system will also incorporate a panic button should the user feel that they need help urgently. Remote tracking in this manner, incorporating remote adjustments (which may be automatic) of the PBM parameters are novel and useful.

Attributes and Capabilities of the Present Invention:

The present invention provides a number of positive attributes, properties, and capabilities. Among them are the following:

1. The present invention can deliver light energy over a wide range for many different parameters, such as but not limited to wavelength, coherency/synchrony, energy (Joules (J)), Power (Watts (W) or milliwatts (mW)) or irradiance (W/cm$^2$), radiant exposure (J/cm$^2$), exposure time (seconds), wave type (continuous or pulse), frequency (Hertz (Hz)), duty cycle (percentage), fraction protocol (number of patient treatment sessions), light beam size (area of landed beam), and light beam penetration (delivery) distance to achieve therapeutic outcomes for the brain and the neural system.

2. The present invention is able to illuminate the various targeted areas of the brain by way of directing the light rays and light wavelengths. In this respect, the wavelengths of light are pre-selected to achieve the desired penetration into the brain materials. This results in improved outcomes for respective neural diseases and disorders.

3. The present invention preferably targets specific cortical hubs of the Default Mode Network (DMN) or other networks, thus aiming to heal lesions in the hubs associated with brain disorders such as Alzheimer's disease and dementia, and other conditions where a DMN or other network dysfunction is a factor.

4. The present invention preferably combines transcranial and intranasal light therapy, wherein: (i) the transcranial headset directs light energy to dorsal/upper areas of the neocortical areas of the brain; and (ii) the intranasal unit directs light energy to the ventral or underside of the brain. A secondary module is preferably added to the sub-occipital area to reach the cerebellum and brain stem. In combination, this provides more comprehensive coverage than current transcranial methods alone and current intranasal methods alone.

5. The present invention provides a lightweight transcranial headset which is more comfortable to use than a full helmet which is used in other transcranial photobiomodulation methods.

6. The present invention provides an easy to use intranasal applicator which can be clipped to the external wall of a nostril while concomitantly inserting an encased solid state electronic light source (such as the light emitting diode or a low level laser diode) within the nasal cavity to deliver the light therapy.

7. The present invention has relatively low electric power requirements.

8. The present invention separates the delivery of light energy from the processing and power controller assembly for both hygiene and cost saving purposes, and also provides for the interchange and substitution of different light generating units with a single processing controller assembly that will convey the appropriate power dosage for this purpose, as well as to interface with a smart phone, smart watch, tablet computer, laptop computer, desktop computer or other computing device.

9. The present invention uses diagnostic tools, such as EEG, to detect brain data in a subject. Such data is useful for selecting specific parameters for PBM treatment of the subject, and in particular, for selecting specific parameters of PBM treatment that will most likely to be effective in treating the subject's specific abnormalities, thus providing a personalized treatment.

10. The present invention intelligently processes the brain data of a subject detected by the diagnostic tool by: (i) comparing the subject's brain data to brain data which is considered to be normal; (ii) evaluating whether there are any abnormalities in the subject's brain data; and (iii) selecting specific parameters for PBM treatment of the subject in view of the abnormalities.

11. The present invention can automatically adjust parameters at the user end to implement the intelligently processed optimum intervention, with an option for manual overrides.

12. The present invention can use telemetry to collect data regarding whether the system is on or off, and the operational parameters used by the system of the present invention, and transmit such data to a base where it can be recorded and monitored.

Study #1:

Study #1 was aimed at evaluating the effect of near-infrared PBM on 5 patients with mild to moderately severe dementia or possible AD using a preferred device of the present invention.

The case series followed the participants over: (i) 12 weeks of active treatment; and (ii) a 4-week follow-up period with no treatment. Patients were administered PBM using an intranasal device at home daily, and were administered transcranial-intranasal PBM at the clinical site on a weekly basis. The near-infrared light (810 nm) was pulsed at 10 Hz frequency via light-emitting diodes (LEDs), delivered to the hubs of the default mode network (DMN).

Figure 10:
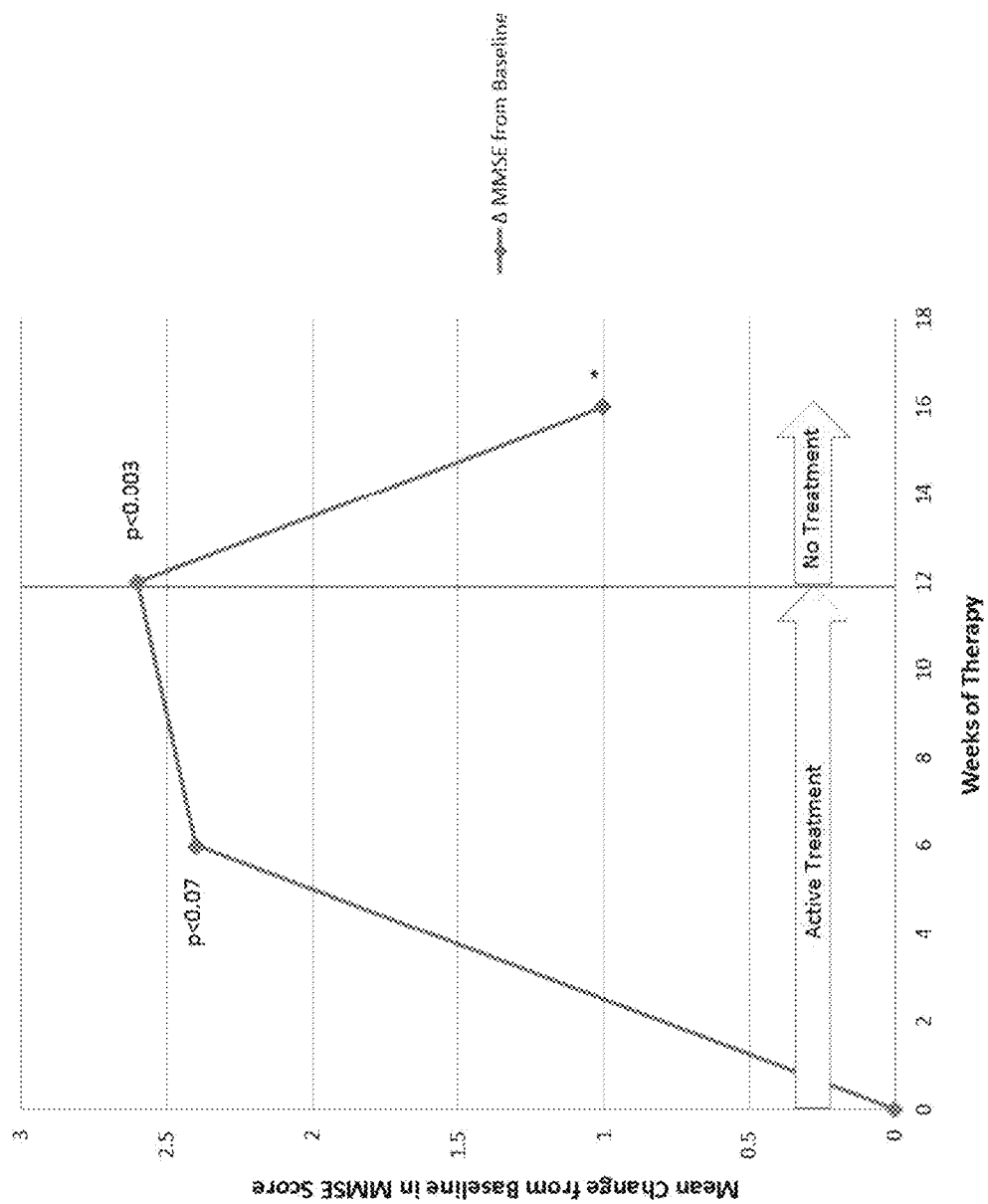
FIG. 10 is a graph showing the mean change from baseline in Mini-Mental State Examination (MMSE) scores in dementia patients in a case report in Study No. 1.

Cognitive impairment was assessed using the MMSE and the ADAS-cog scales. Following 12 weeks of treatment with PBM, significant improvement in cognition was observed, as assessed using the MMSE (p<0.003) and ADAS-cog (p<0.023). See FIG. 10 for the MMSE scores. The 12-week treatment also resulted in increased function, better sleep, reduced anxiety and fewer angry outbursts. No adverse effects were reported. Furthermore, significant declines in cognitive functioning were observed during the 4-week no-treatment period, suggesting that maintenance treatment would be important. This study demonstrated that PBM can produce significant improvements in cognition in patients with mild to moderately severe dementia and possible AD.

Study #2:

For Study #2, certain modifications were made to the protocols of the earlier Study #1, including: (i) the pulse rate was changed from 10 Hz (alpha) to 40 Hz (gamma); (ii) a randomly selected patient with moderate Alzheimer's disease was given the headset to use at home for once a night, 6 nights a week; (iii) fewer LEDs were used, but more precisely targeted at the hubs of the DMN with more power.

The outcomes were even more significant than what was observed with the participants of Study #1. Significant behavioral changes were already observed from the second day of treatment, such as improvement in eye contact from 1/10 to 9.2/10. By the second day, the patient was emerging from silence and starting to hold meaningful conversations, and was able to write. By the third week, he had regained most of his quality of life, with much improved ability to communicate. See FIG. 11.

Figure 12:
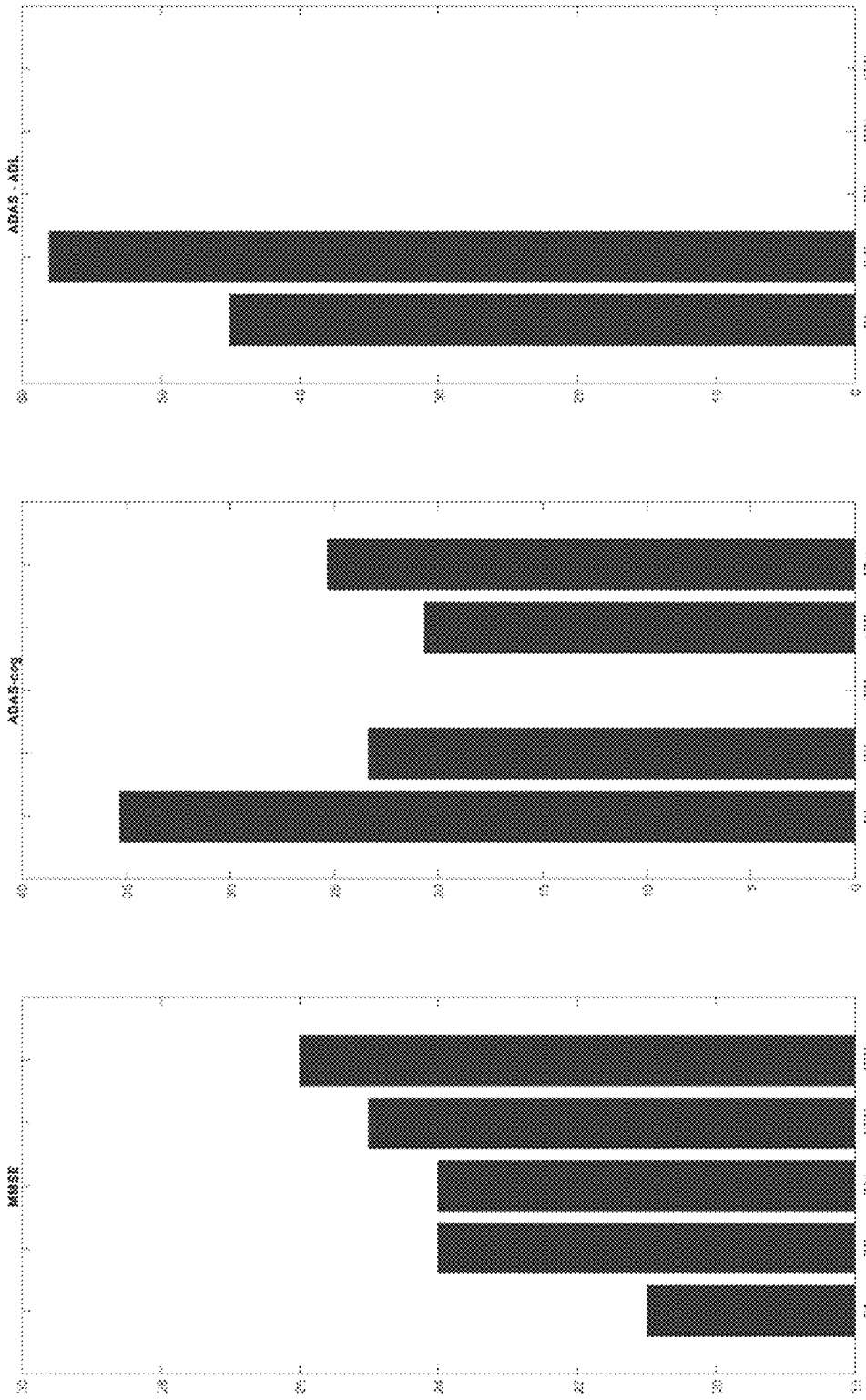
FIG. 12 comprises bar charts showing MMSE, Alzheimer's Disease Assessment Scale-cognitive (ADAS-cog) and Alzheimer's Disease Cooperative Study-Activities of Daily Living (ADCS-ADL) scores in Study No. 2.

Investigators in this study reported data over a total of 17 weeks. As presented in FIG. 12, Mini Mental Status Examination (MMSE) increased from 21 at baseline to 26 at Week 17, and Alzheimer's disease Assessment Scale-cognitive subscale (ADAS-cog) improved from 35 to 25. They covered data over 3 weeks for the ADCS-ADL scores, which showed improvements from 43 to 58.

Figure 13:
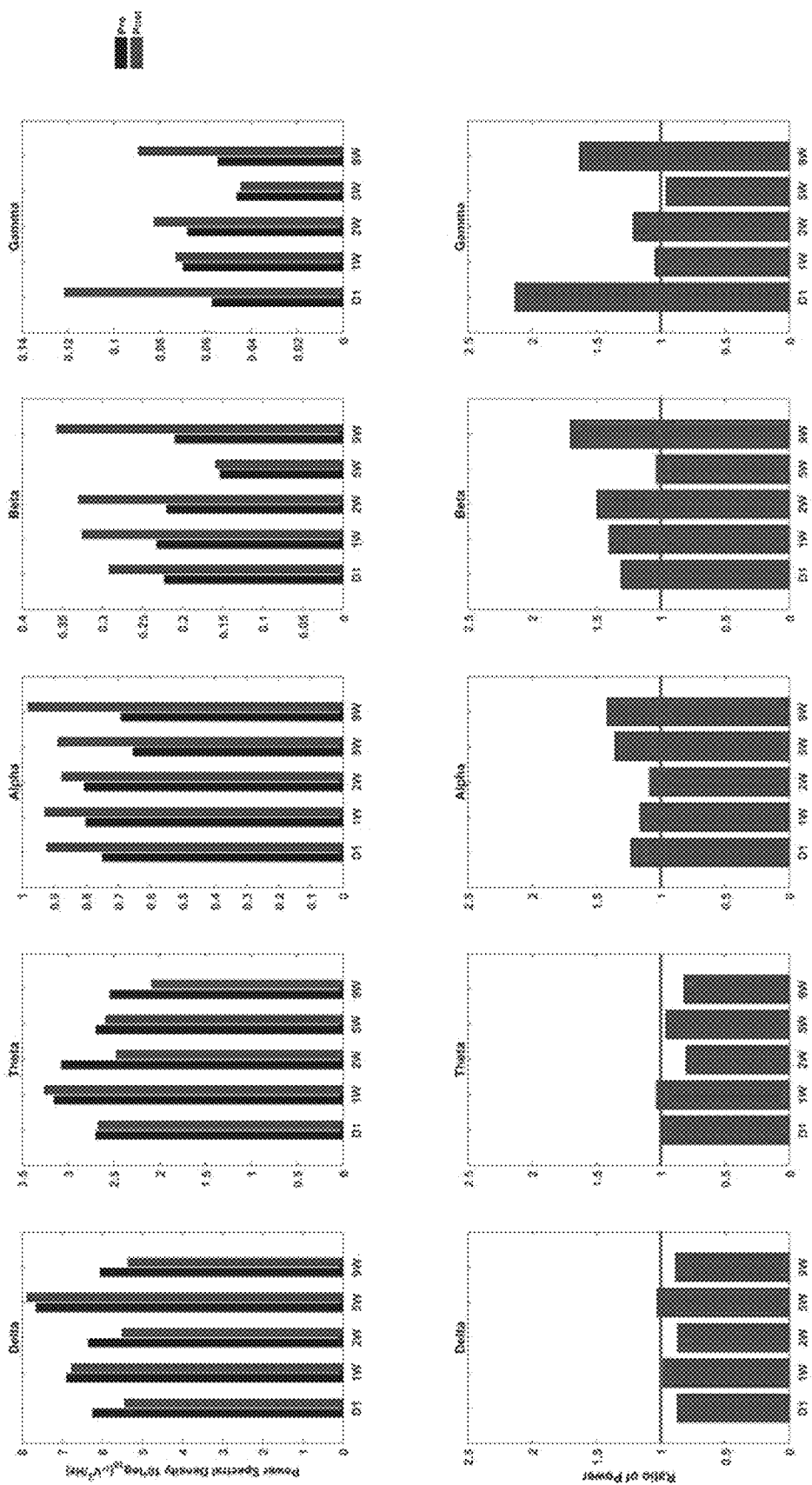
FIG. 13 comprises bar charts showing acute short-term changes in brain oscillations after a single PBM session in Study No. 2.

During each PBM treatment, using EEG to measure neural oscillations, significant elevation in the power spectrum of the higher frequency oscillations in gamma, beta and alpha were observed. On the other hand, the power spectrum of the theta and delta oscillations were reduced. See FIG. 13. It should be noted that this study utilized a sham device in the Week 5 measurement, and there was no change in the gamma and beta power spectral density, which supports the theory that the brain responds to an active (but not to a sham) device. The change in alpha oscillations were expressed partly because the subject closed his eyes at resting state during the sessions.

In Study #2, delivery of near infrared light at 810 nm to the hubs of the DMN, pulsed at 40 Hz produced significant improvements in:
  cognition (measured over 17 weeks)
  daily living and quality of life factors (measured over 3 weeks)
  electrophysiological baseline power over 3 weeks, across all oscillations
  acute short-term entrainment after each treatment, elevating the power of gamma, beta and alpha oscillations; and attenuating the power of theta and delta oscillations.

Outcomes were rapid and significant, continuous and sustained over 3 weeks. The metrics continued to improve over the 17 weeks of the study. No negative side effects were observed.

In summary, when delivering 810 nm pulse at 40 Hz, the investigators were able to significantly improve EEG signatures associated with AD and produce significant improvements in the cognition measures provided by the MMSE and the ADAS-cog measures.

Study #3:

In Study #3, patients randomized to an immediate treatment (IM) group were given a preferred device of the present invention to use at home. Patients randomized to a wait-list (WL) group were followed for 12 weeks of their usual (non-PBM) care. Eight patients with dementia completed the pilot trial, where four patients were randomized to the IM group and four were randomized to WL. The two groups did not differ significantly on demographic variables or MMSE at baseline. Unlike the previous studies, the frequency of PBM treatments was once every other day for 12 weeks.

Figure 14:
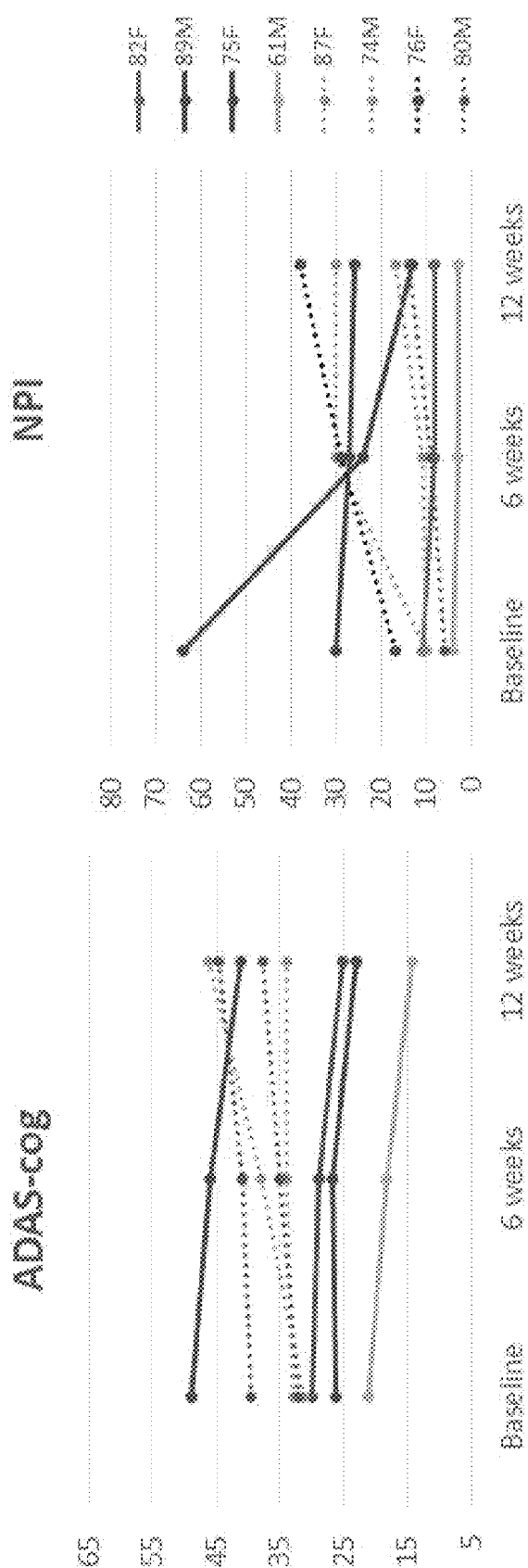
FIG. 14 comprises graphs showing ADAS-cog and Neuropsychiatric Inventory (NPI) behavior changes for dementia patients receiving 12 weeks of PBM treatment and for patients receiving usual care in Study No. 3.

After 12 weeks, patients randomized to the IM group experienced significant improvements in cognitive function (using ADAS-cog) and behavioral symptoms (using Neuropsychiatric Inventory (NPI), see FIG. 14). In contrast, cognition and behavioral symptoms declined in the WL subjects. A repeated measures ANCOVA, with group (IM vs. WL) as the between-subject measure, time (baseline, 6- and 12-weeks) as the with-in subject measure and age, education and baseline MMSE as covariates revealed a significant group by time interaction for ADAS-cog (F1,3=33.35, p=0.01) and NPI (F1,3=18.01, p=0.02).

Figure 15:
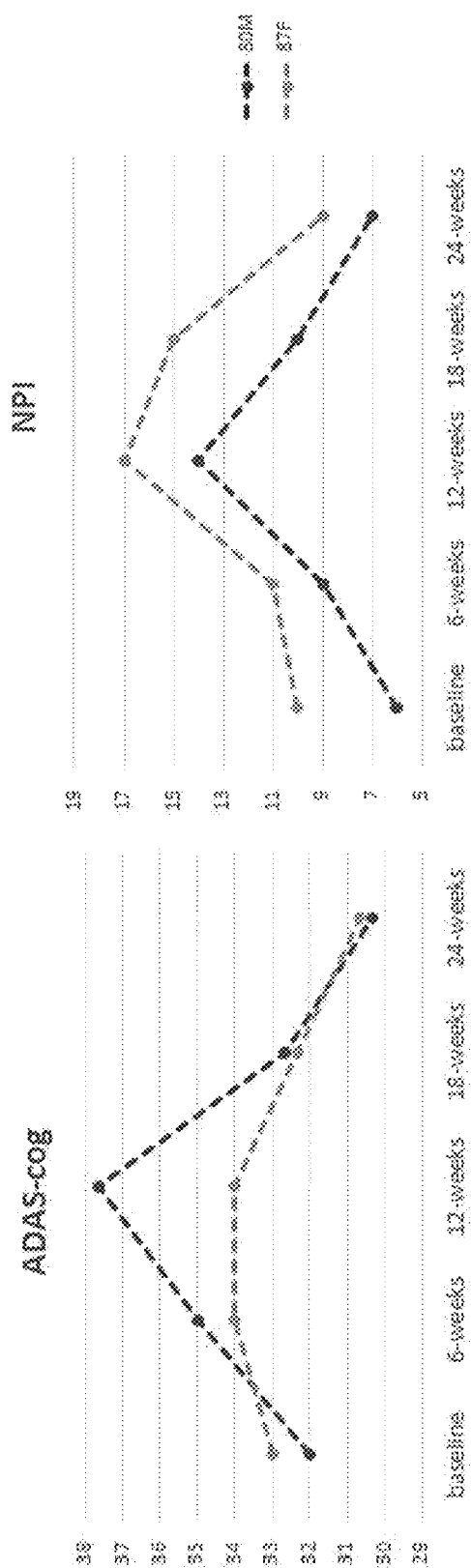
FIG. 15 comprises graphs showing ADAS-cog and NPI behavior changes for dementia patients before and after 12 weeks of regular PBM treatments in Study No. 3.

WL subjects had the option of receiving 12 weeks of PBM treatments after completing 12 weeks of their usual care. Cognitive and behavioral assessments were re-assessed at 18 and 24-weeks, however these subjects did not undergo further MRIs. FIG. 15 shows that 2 WL subjects, who declined during 12 weeks of usual care, improved cognitively and behaviorally after they started to use the device of the present invention (indicated in FIG. 15). Paired t-tests revealed significant differences in NPI scores at baseline and 12-weeks (t=−15.0, df=1, p=0.04), at 12- and 24-weeks (t=15.0, df=1, p=0.04), but not at baseline and 24-weeks (t=0.0, df=1, p=1.0) in these 2 WL subjects. Although paired t-test revealed no significant difference in ADAS-cog scores from baseline to 12-weeks, 12- to 24-weeks, or from baseline to 24-weeks, FIG. 15 suggests this is because the female WL subject's ADAS-cog scores changed minimally over the 24 weeks. Nevertheless, it is noteworthy that her ADAS-cog score after 12 weeks of using the device (30.67 at 24 weeks) was lower (i.e., better) than at it was at baseline.

Figure 16A:
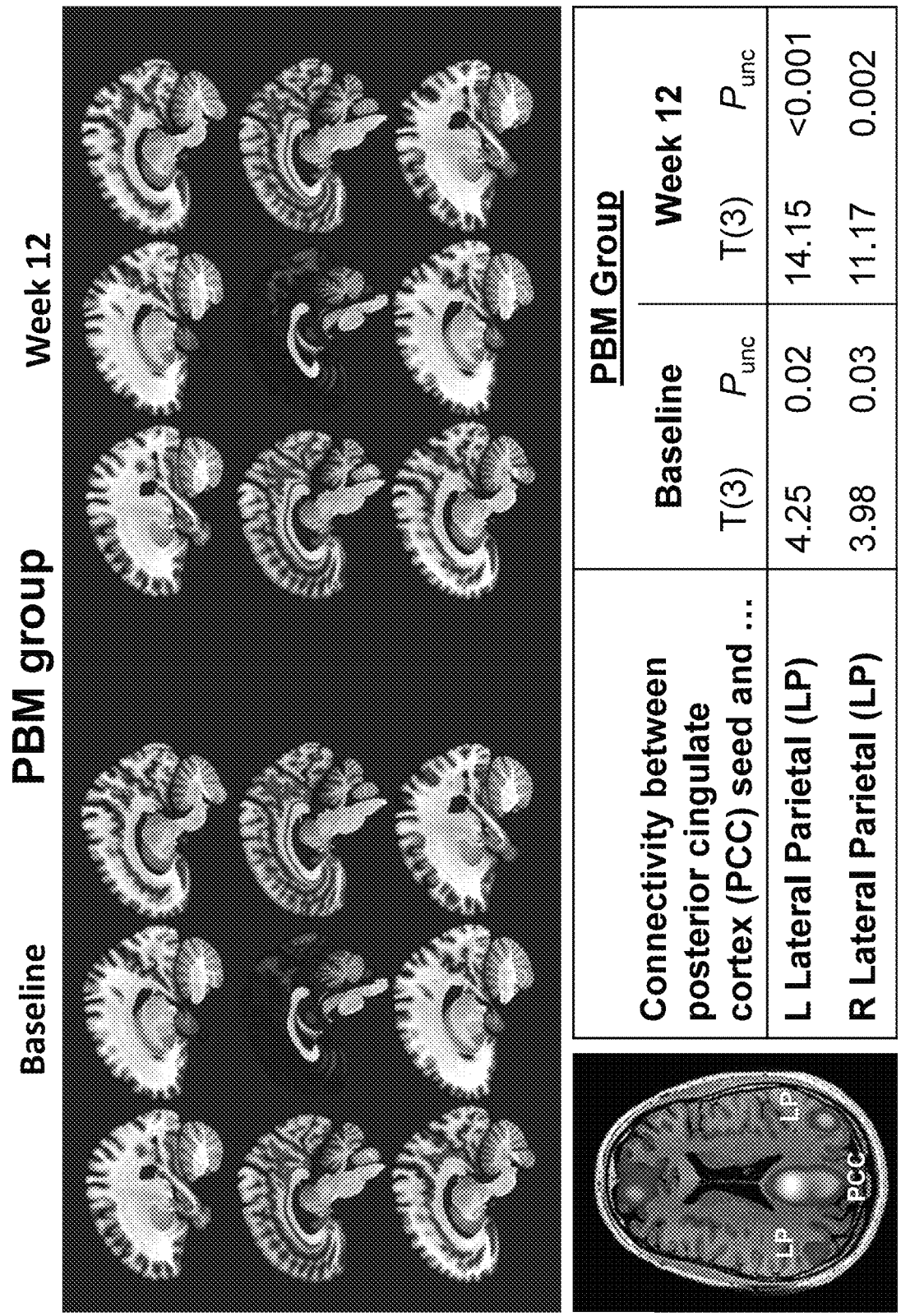
FIGS. 16A and 16B comprise functional magnetic resonance imaging (fMRI) for dementia patients before and after 12 weeks of regular PBM treatments in Study No. 3.
Figure 16B:
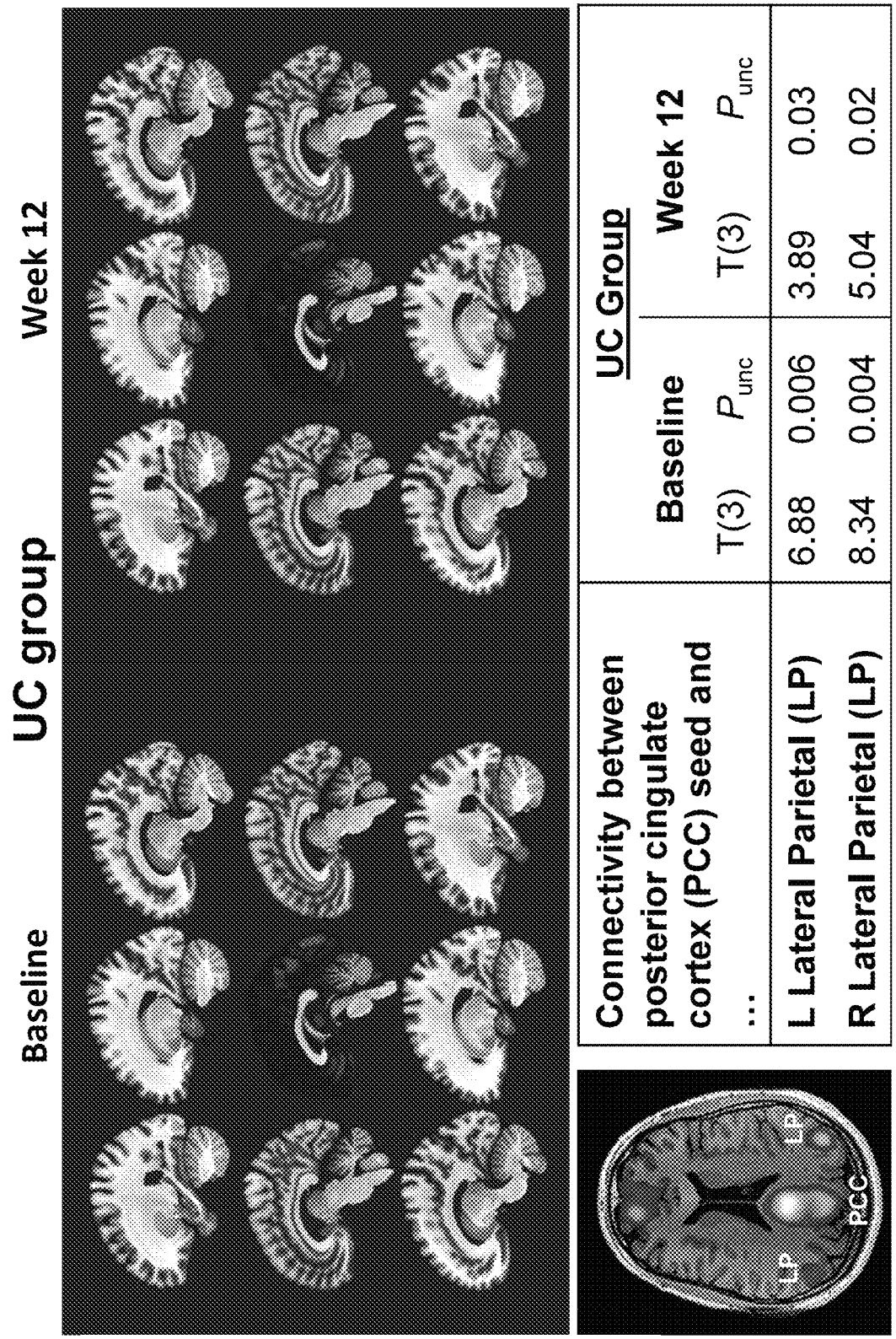

After 12 weeks of PBM treatments, there was increased perfusion in the posterior cingulate and bilateral parietal cortex inferior temporal, and left frontal cortex. There was also increased functional connectivity within DMN in the 4 IM patients. Specifically, there was greater connectivity between the hippocampus, lateral parietal cortex, and posterior cingulate cortex in the IM group at week 12 compared to baseline. FIGS. 16A and 16B comprise functional magnetic resonance imaging (fMRI) for dementia patients before and after 12 weeks of regular PBM treatments.

Study #4:

A double-blind EEG study was carried out on 20 healthy subjects using a preferred device of the present invention, aiming to observe whether the electrophysiological changes is replicated in healthy brains, and hence confirming the intervention quality of the invention. The active and sham versions of the device were used for a 20-minute session. The power spectrum and connectivity analyses were performed to assess the difference in the induced change between active and sham intervention.

Figure 17:
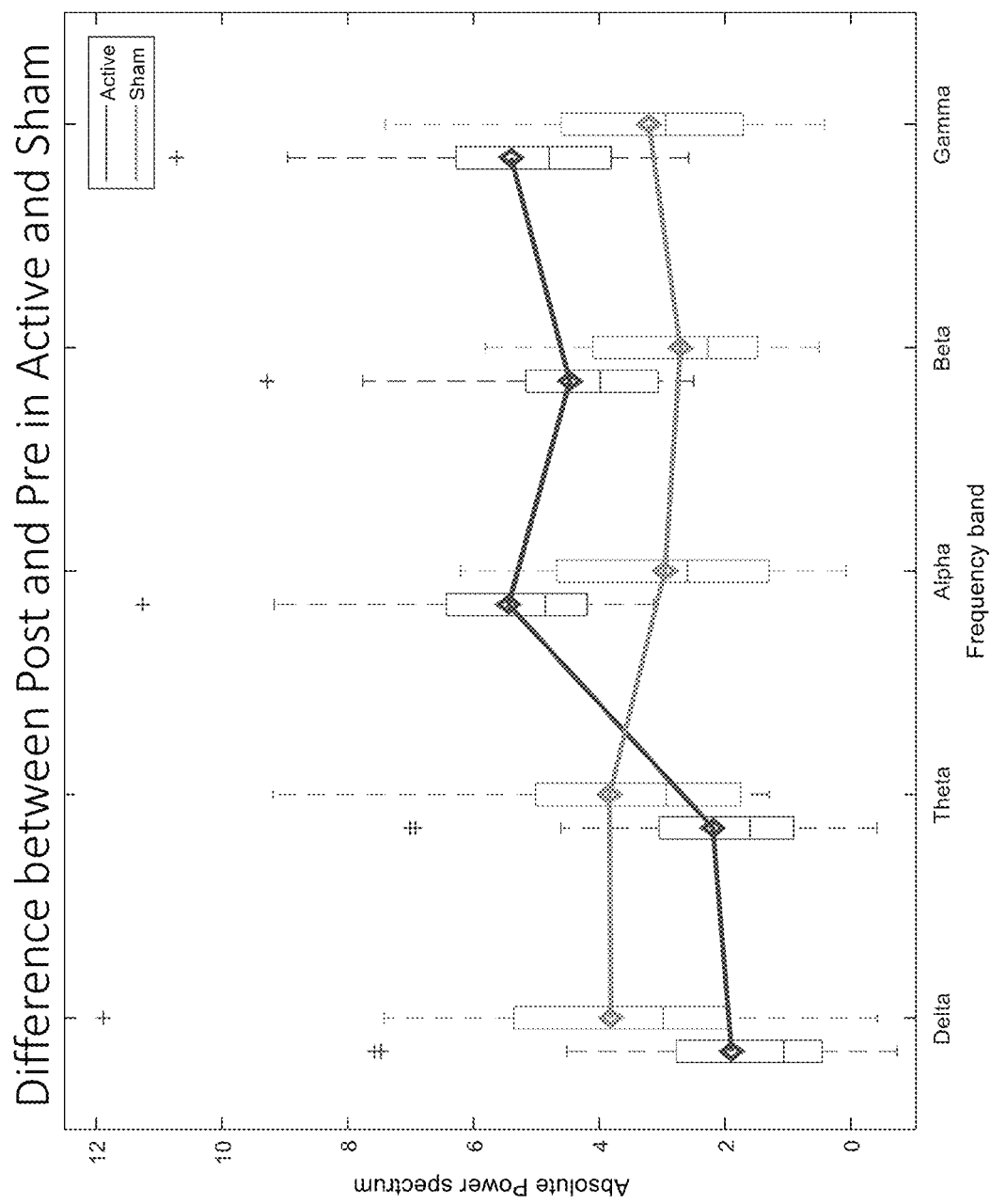
FIG. 17 comprises a summary of changes in the power spectrum for healthy subjects before and after receiving PBM treatments after a single session in Study No. 4.
Figure 18:
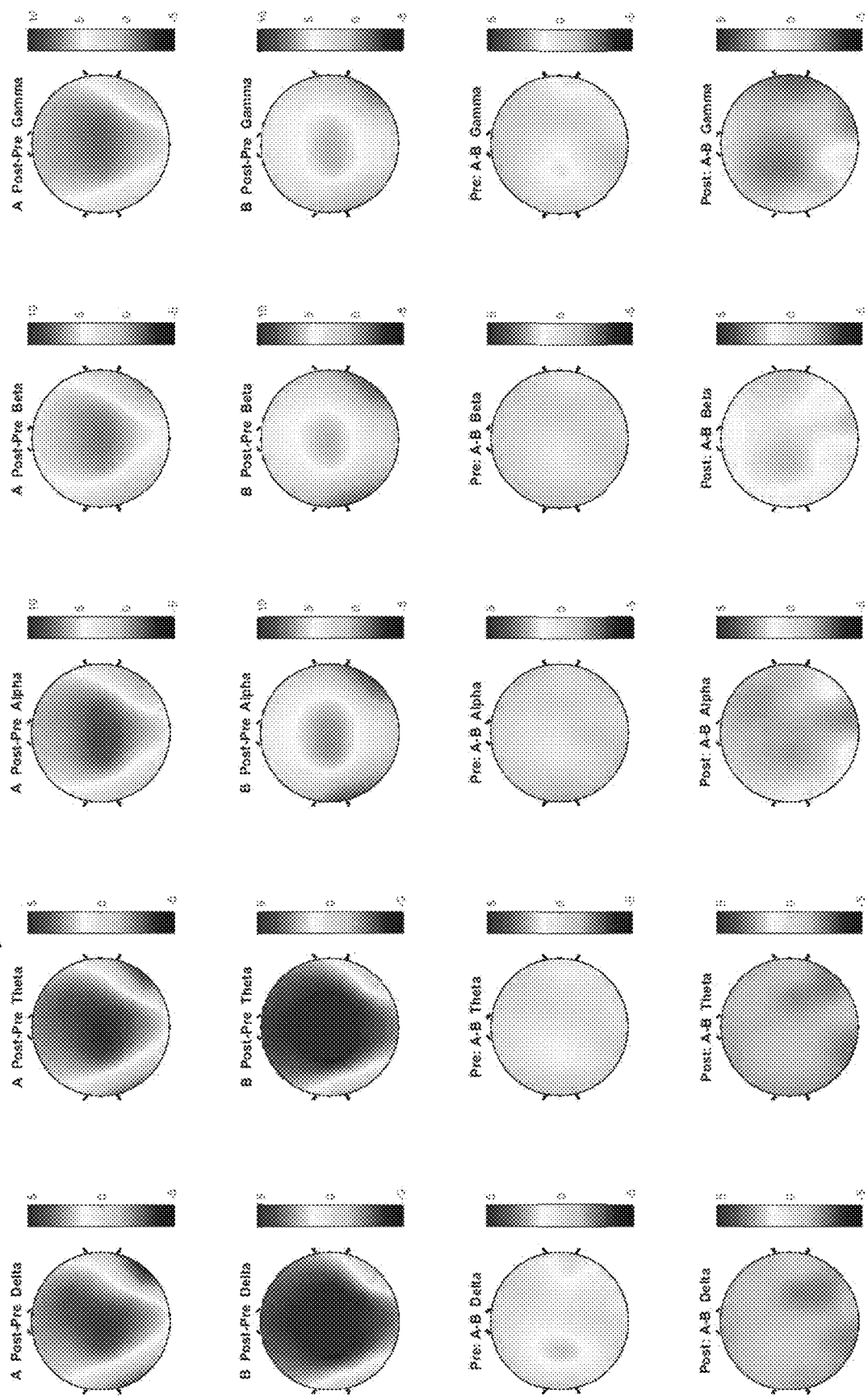
FIG. 18 illustrates the changes in the power spectrum for healthy subjects illustrated in brain maps comparing with sham in Study No. 4.
Figure 19:
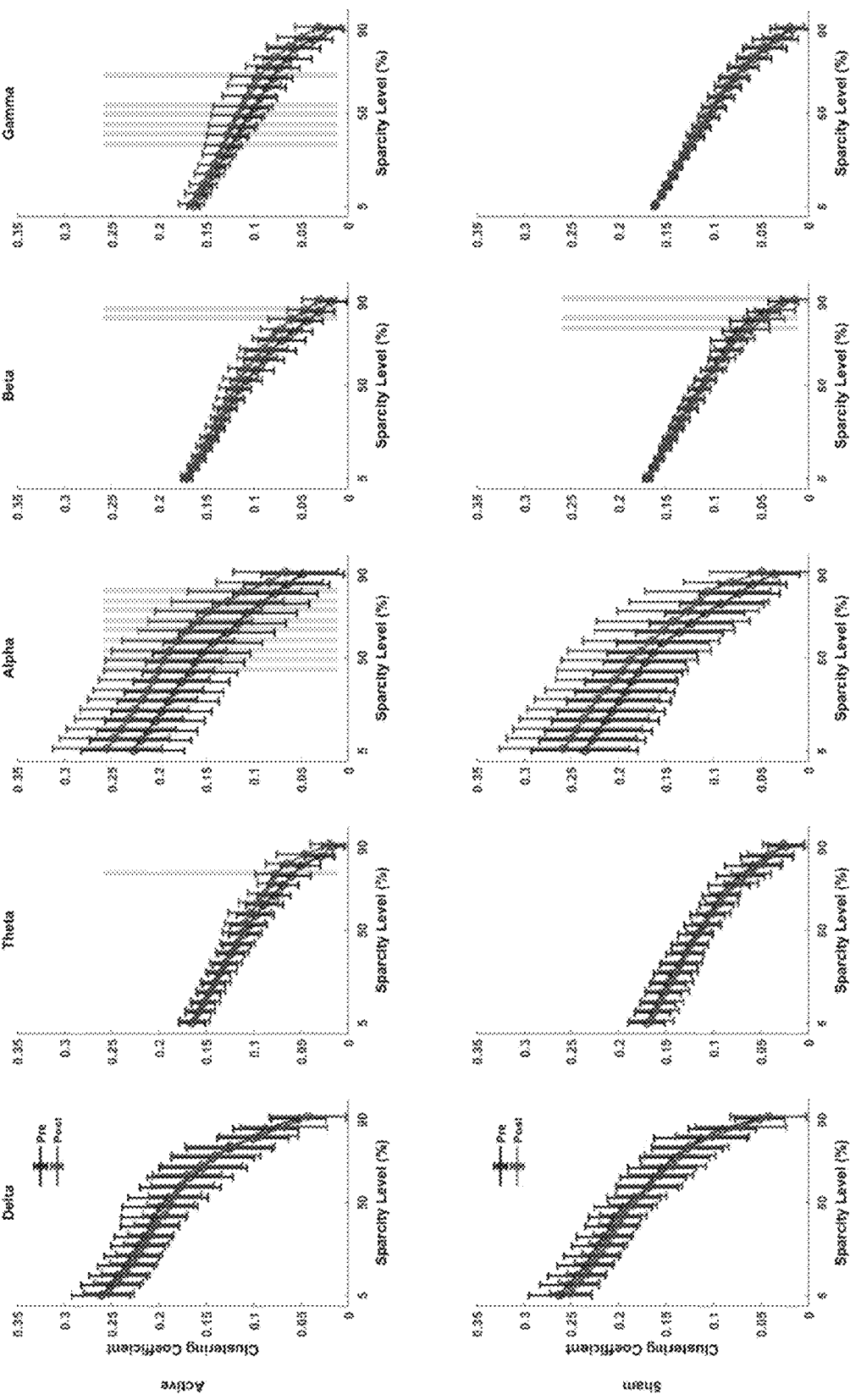
FIG. 19 comprises changes in significance in connectivity, using graph theory to measure clustering coefficient for various sparsity levels in Study No. 4.

FIG. 17 comprises a summary of changes in the power spectrum for healthy subjects before and after receiving PBM treatments after a single session. FIG. 18 illustrates the changes in the power spectrum for healthy subjects illustrated in brain maps comparing with sham. FIG. 19 comprises changes in significance in connectivity, using graph theory to measure clustering coefficient for various sparsity levels in Study No. 4.

The analysis revealed that PBM delivered by the device produced frequency dependent effects on endogenous brain activity. A reduction of low-frequency power (i.e., delta and theta) and an increase of high-frequency power (i.e., alpha, beta, and gamma) were observed following active stimulation. Comparison between active and sham groups demonstrated a significant difference in delta 1-4 Hz; $t=-2.53$ $p=0.0203$), theta (4-7 Hz; $t=-3.18$ $p=0.0049$), alpha (8-12 Hz; $t=4.26$ $p=0.0004$), beta (12-30 Hz; $t=3.02$ $p=0.0070$), and gamma (30-50 Hz; $t=3.84$, $p=0.0011$). The weighted phase lag index (wPLI) and graph theory measures revealed significant change ($p<0.001$) between active and sham stimulation, limited to the alpha and gamma frequencies. Findings from this study provide evidence that PBM modulates cortical oscillations that impact brain connectivity in a pulse frequency-dependent manner. The study confirms that near infrared light with the right parameters can penetrate the brain sufficiently enough to produce significant electrophysiological changes.

Although the computer applications described above have been described separately, it should be understood that any two or more of the applications disclosed herein can be combined in any combination. Any of the applications described herein can include machine-readable instructions for execution by: (a) a processor, (b) a controller, and/or (c) any other suitable processing device. Any application, algorithm or software disclosed herein can be embodied in software stored on a non-transitory tangible medium such as, for example, a flash memory, a CD-ROM, a floppy disk, a hard drive, a digital versatile disk (DVD), or other memory devices, but persons of ordinary skill in the art will readily appreciate that the entire application and/or parts thereof could alternatively be executed by a device other than a controller and/or embodied in firmware or dedicated hardware in a well-known manner (e.g., it may be implemented by an application specific integrated circuit (ASIC), a programmable logic device (PLD), a field programmable logic device (FPLD), discrete logic, etc.). Further, persons of ordinary skill in the art will readily appreciate that many other methods of implementing the example machine readable instructions may alternatively be used.

The scope of the claims should not be limited by the preferred embodiments set forth in the examples, but should be given the broadest interpretation consistent with the description as a whole.

The invention claimed is:

1. A system for performing non-invasive photobiomodulation (PBM) therapy of a living human brain of a subject, said non-invasive PBM system comprising:
(A) one or more configured irradiation units, each of said one or more configured irradiation units comprising:
a portable hollow casing having fixed dimensions, a sized internal spatial volume and an external surface configuration suitable for application to a skull of the subject, said portable hollow casing being comprised of a light energy transmitting material which forms at least a portion of the configured external surface of said portable hollow casing; and
at least one light generating unit housed and contained within said sized internal spatial volume of said portable hollow casing of each configured irradiation unit and which is capable of generating light energy sufficient to irradiate the skull and penetrate through the skull to pass into the brain,
whereby said one or more configured irradiation units emit the light energy after application to the skull and achieve passage of said emitted light energy into and through the skull into at least one portion of the brain in-vivo;
(B) a frame adapted for support of said one or more configured irradiation units and for at will placement of said light energy transmitting external surface of said one or more configured irradiation units at a fixed position and desired irradiation direction on the skull;
(C) a configured irradiation lens comprising:
a portable hollow casing having fixed dimensions, a sized internal spatial volume, and an external surface configuration suitable for in-vivo insertion into a nasal cavity space of a nostril without causing substantial impairment to an ability of the subject to breathe and without invading nasal tissues of the subject, said portable hollow casing being comprised of a light energy transmitting material which forms at least a portion of the configured external surface of said portable hollow casing; and
at least one light generating unit housed and contained within said sized internal spatial volume of said portable hollow casing and which is capable of generating light energy sufficient to penetrate through the nasal tissues and to pass into the brain,
whereby said configured irradiation lens emits the light energy in any desired direction within the nasal cavity after in-vivo insertion and achieve passage of said emitted light energy from the nasal cavity into at least one portion of the brain in-vivo;
(D) a self-administrable applicator means adapted for support of said configured irradiation lens and for at will placement of said light energy transmitting external surface of said portable hollow casing of said configured irradiation lens at a fixed position and desired irradiation direction within the nostril adjacent to an internal lining of the nasal cavity of the subject;
(E) a replenishable power source of direct electrical current; and
(F) a portable controller assembly able to control delivery of the light energy from said one or more configured irradiation units and said configured irradiation lens into at least one portion of the brain in-vivo,
said portable controller assembly comprising:
(i) a receiving circuit for receipt of such direct electrical current as is transferred to the portable controller assembly from the power source;

(ii) a central processing unit for controlling and directing the flow of such direct electrical current as is received by the receiving circuit;
(iii) a delivery circuit for delivering such direct electrical current from the controller assembly to said one or more configured irradiation units and said configured irradiation lens;
(iv) at least one connector in electrical communication with the power source for conveyance of such direct electrical current to the central processing unit; and
(v) at least one connector in electrical communication with said one or more configured irradiation units for conveyance of such direct electrical current from said central processing unit to said one or more configured irradiation units and said configured irradiation lens,
wherein the portable controller assembly controls the light energy emitted from said one or more configured irradiation units and said configured irradiation lens with respect to one or more operational parameters selected from the group consisting of: wavelength, coherency, energy, power, radiant exposure, exposure time, wave type, pulse frequency, fraction protocol, duty cycle, light beam spot and light beam penetration distance;
further comprising:
a diagnostic tool for collecting brain activity data from the subject; and
a first computing device communicatively coupled to said diagnostic tool, said first computing device being selected from the group consisting of a smart phone, a smart watch, a tablet computer, a laptop computer and a desktop computer, wherein said computing device has an analysis software application installed thereon;
wherein the diagnostic tool transmits said collected brain activity data to the first computing device;
wherein the analysis software application analyzes said collected brain activity data by comparing it to brain activity data of normal subjects and, based on this comparison, produces analysis data of the subject's brain activity;
a photobiomodulation (PBM) parameter-setting software application which is installed on said first computing device or a second computing device communicatively coupled to said first computing device, said second computing device being selected from the group consisting of a smart phone, a smart watch, a tablet computer, a laptop computer and a desktop computer;
wherein said analysis data of the subject's brain activity is transmitted to or retrieved by the PBM parameter-setting software application;
wherein, based on said analysis data of the subject's brain activity, the PBM parameter-setting software application adjusts the one or more operational parameters of the light energy; and
wherein instructions regarding the adjusted one or more operational parameters of the light energy are transmitted to the portable controller assembly, to direct the light energy with the adjusted one or more operational parameters to the subject;
wherein the diagnostic tool, first computing device, analysis software application, second computing device and PBM parameter-setting software application are used concurrently with the system providing PBM therapy by emitting light energy to the subject, thus: (a) automatically producing the analysis data of the subject's brain activity in real-time; and (b) automatically adjusting the one or more operational parameters of the light energy in real-time and at the same time as performing PBM therapy.

2. The system of claim 1, wherein said one or more configuration units are positioned to direct light energy to one or more regions of the brain selected from the group consisting of:
the ventral medial prefrontal cortex (vmPFC), the dorsal medial prefrontal cortex (dmPFC), the posterior cingulate cortex (PCC), the precuneus (PCu), the lateral parietal cortex (LPC), the entorhinal cortex (EC), right dorsal-lateral prefrontal cortex (DLPC), left dorsal-lateral prefrontal cortex (DLPC), cerebellum and brain stem; and
wherein said configured irradiation lens is positioned to direct light energy, via the nasal cavity, to one or more regions of the brain selected from the group consisting of: ventral prefrontal cortex, entorhinal cortex and parahippocampal area.

3. The system of claim 1, wherein the transmission or retrieval of said analysis data by the PBM parameter-setting software application, the adjustment of the one or more operational parameters of the light energy by the PBM parameter-setting software application, and the transmission of instructions regarding the adjusted one or more operational parameters of light energy to the portable controller assembly are automated to provide the subject with customized PBM therapy.

4. The system of claim 1, further comprising a database communicatively coupled to said first computing device or said second computing device, wherein said database stores data selected from the group consisting of the collected brain activity data, the analysis data of the subject's brain activity and data on the adjusted one or more operational parameters of the light energy.

5. The system of claim 1, wherein the diagnostic tool is selected from the group consisting of a functional magnetic resonance imaging (fMRI) device, a functional Near-Infrared Spectroscopy (fNIRS) device, a Magnetoencephalography (MEG) device and an Electroencephalography (EEG) device.

6. The system of claim 5, wherein the diagnostic tool is an EEG device;
wherein, when the EEG device detects that the subject's brain waves are abnormally in phase at two different locations in the brain or two different brain networks or sub-networks, one or more of the configured irradiation units are positioned to target at least one of these two locations in the brain or at least one of these two brain networks or sub-networks, and the portable controller assembly controls the one or more operational parameters of the light energy to cause the subject's brain waves go out of phase with each other at the two different locations or the two different brain networks or sub-networks.

7. The system of claim 5, wherein the diagnostic tool is an EEG device;
wherein, when the EEG device detects that the subject's brain waves are abnormally out of phase at two different locations in the brain or two different brain networks or sub-networks, one or more of the configured irradiation units are positioned to target at least one of these two locations in the brain or at least one of these two brain networks or sub-networks, and the portable controller assembly controls the one or more operational parameters of the light energy to cause the subject's brain waves go closer to being in phase with each other at the two different locations or the two different brain networks or sub-networks.

8. The system of claim 1, wherein the one or more operational parameters is pulse frequency, and wherein the portable controller assembly controls the pulse frequency to an alpha pulse frequency for the treatment of a condition selected from the group consisting of traumatic brain injury (TBI), depression, anxiety, hypoxia, stroke and conditions responsive to increased power and connectivity in alpha oscillations.

9. The system of claim 8, wherein the alpha pulse frequency is about 10 Hz.

10. The system of claim 1, wherein the one or more operational parameters is pulse frequency, and wherein the portable controller assembly controls the pulse frequency to a gamma pulse frequency for the treatment of a condition selected from the group consisting of Alzheimer's Disease, Parkinson's Disease, attention deficit hyperactivity disorder (ADHD), autism and schizophrenia.

11. The system of claim 10, wherein the gamma pulse frequency is about 40 Hz.

12. The system of claim 1, wherein the portable controller assembly controls the pulse frequency to an alpha pulse frequency for the improvement of the subject's athletic performance.

13. The system of claim 12, wherein the alpha pulse frequency is about 10 Hz.

14. The system of claim 1, wherein the one or more operational parameters is pulse frequency, and wherein the portable controller assembly controls the pulse frequency to a gamma pulse frequency for the improvement of the subject's cognitive abilities or the subject's athletic performance.

15. The system of claim 14, wherein the gamma pulse frequency is about 40 Hz.

16. The system of claim 1, wherein the one or more operational parameters is pulse frequency, and wherein the portable controller assembly controls the pulse frequency to a pulse frequency for helping the subject reach a high-level meditative state.

17. The system of claim 16, wherein the pulse frequency is about 40 Hz to 1000 Hz or higher.

18. The system of claim 1, wherein the system acts as a telemeter, whereby data on the one or more operational parameters of the light energy is transmitted to, recorded and monitored at a base.

\* \* \* \* \*